US009840465B2

(12) United States Patent
Kolocouris et al.

(10) Patent No.: US 9,840,465 B2
(45) Date of Patent: Dec. 12, 2017

(54) ANTIVIRAL COMPOUNDS

(71) Applicant: Brigham Young University, Provo, UT (US)

(72) Inventors: Antonios Kolocouris, Athens (GR); David D. Busath, Orem, UT (US); Brent Johnson, Orem, UT (US)

( * ) Notice: Subject to any disclaimer, the term of this patent is extended or adjusted under 35 U.S.C. 154(b) by 0 days.

(21) Appl. No.: 14/765,539

(22) PCT Filed: Feb. 2, 2014

(86) PCT No.: PCT/US2014/014359
§ 371 (c)(1),
(2) Date: Aug. 3, 2015

(87) PCT Pub. No.: WO2014/121170
PCT Pub. Date: Aug. 7, 2014

(65) Prior Publication Data
US 2015/0368196 A1    Dec. 24, 2015

Related U.S. Application Data

(60) Provisional application No. 61/920,359, filed on Dec. 23, 2013, provisional application No. 61/760,060, filed on Feb. 2, 2013.

(51) Int. Cl.
| | |
|---|---|
| C07D 209/96 | (2006.01) |
| C07D 221/20 | (2006.01) |
| C07D 207/06 | (2006.01) |
| C07D 211/10 | (2006.01) |
| C07C 211/38 | (2006.01) |

(52) U.S. Cl.
CPC .......... *C07D 209/96* (2013.01); *C07C 211/38* (2013.01); *C07D 207/06* (2013.01); *C07D 211/10* (2013.01); *C07D 221/20* (2013.01); *C07C 2601/14* (2017.05); *C07C 2603/74* (2017.05)

(58) Field of Classification Search
CPC ................................................. C07D 209/96
See application file for complete search history.

(56) References Cited

U.S. PATENT DOCUMENTS

2011/0201665 A1    8/2011  Altmeyer et al.
2012/0270917 A1    10/2012 DeGrado et al.

FOREIGN PATENT DOCUMENTS

WO    WO 2011/022191 A1    2/2011

OTHER PUBLICATIONS

Kalir, et al. Document No. 96:85108, retrieved from CAPLUS; (1981).*
HIV/AIDS [online] retrieved from the internet on Sep. 11, 2011 URL; (http://www.mayoclinic.com/health/hiv-aids/DS00005).*
SARS [online] retrieved from the internet on Sep. 11, 2011 URL; (http://www.emedicinehealth.com/script/main/art.asp?articlekey=137335).*
Duque, Maria D., et al., "Inhibitors of the M2 channel of influenza A virus," *Recent Advances in Pharmaceutical Sciences*, pp. 35-64 (2011).
Elefthera Tos, Stelios, et al., "Interaction of aminoadamantane derivatives with the influenza A virus—M2 channel-Docking using a pore blocking model," *Bioorganic & Medicinal Chemistry Letters*, 20:4182-4187 (2010).
International Search Report and Written Opinion for International Application No. PCT/US2014/014359, dated Aug. 13, 2014 (14 pages).
Lundahl, K., et al., "Synthesis and Antiviral Activities of Adamantane Spiro Compounds. 1. Adamantane and Analogous Spiro-3'-pyrrolidines," *Journal of Medicinal Chemisry*, 15(2):129-132 (1972).
Pubchem CID-66645766, 1 page (Nov. 30, 2012).
Scholtissek, C., et al., "How to overcome resistance of influenza A viruses against adamantine derivatives," *Antiviral Research*, 37:83-95 (1998).
Wang, Jun, et al., "Molecular Dynamics Simulation Directed Rational Design of Inhibitors Targeting Drug-Resistant Mutants of Influenza A Virus M2," *J. Am. Chem. Soc.*, 133:12834-12841 (2011).
Balgi, Aruna D., et al., "Inhibitors of the Influenza A Virus M2 Proton Channel Discovered Using a High-Throughput Yeast Growth Restoration Assay," *PLOS ONE*, 8(2):e55271, 9 pages (Feb. 2013).
Gkeka, Paraskevi, et al., "Free Energy Calculations Reveal the Original of Binding Preference for Aminoadamantane Blockers of Influenza A/M2TM Pore," *Journal of Chemical Theory and Computation*, 9(2):1272-1281 (2012).
Kalir, A., et al., "2-Phenyl-2-adamantanamine hydrochloride," *Organic Syntheses* 60:104-108 (1981).
Supplementary European Search Report for related European Application No. 14746650.2, dated Aug. 8, 2016 (6 pages).
Torres, Eva., et al., "Synthesis and Anti-influenza A Virus Activity of 2,2-Dialkylamantadines and Related Compounds," *ACS Medicinal Chemistry Letters*, 3(12):1065-1069 (2012).
Tran, Linh, et al., "Discovery of Potential M2 Channel Inhibitors Based on the Amantadine Scaffold via Virtual Screening and Pharmacophore Modeling," *Molecules*, 16(12):10227-10255 (2011).

* cited by examiner

*Primary Examiner* — Shawquia Jackson
(74) *Attorney, Agent, or Firm* — Brinks Gilson & Lione; Ryan L. Marshall

(57) ABSTRACT

Compounds useful for treating and preventing viral infections including influenza are disclosed. Methods of treating or preventing viral infections, including influenza A infections are disclosed. Specifically, aminoadamantane derivatives that are structurally analogous to amantadine, including spirocyclic compounds, are provided for the treatment of amantadine-insensitive influenza infection in a subject.

13 Claims, 2 Drawing Sheets

ANTIVIRAL COMPOUNDS

REFERENCE TO EARLIER FILED APPLICATIONS

This application claims the benefit under 35 U.S.C. §119 (e) of U.S. Provisional Patent Application No. 61/760,060, filed Feb. 2, 2013, and to U.S. Provisional Patent Application No. 61/920,359, filed Dec. 23, 2013, both titled "ANTIVIRAL COMPOUNDS," which are incorporated, in their entireties, by this reference.

STATEMENT OF GOVERNMENT RIGHTS

The invention was made with government support under U.S. National Institutes of Health grant number AI023007. The United States government has certain rights in the invention.

TECHNICAL FIELD

The present disclosure includes compounds and methods for preventing or treating viral infections and in particular influenza A amantadine-insensitive strains.

BACKGROUND

Influenza, commonly known as the flu, is an infectious disease of birds and mammals caused by RNA viruses of the family Orthomyxoviridae, also known as the influenza viruses. Influenza spreads across the world in seasonal epidemics, resulting in millions of yearly cases of severe illness and hundreds of thousands of yearly deaths. In some outbreaks, the infection rates become pandemic. Often, new influenza strains appear when an existing flu virus spreads to humans from another animal species, or when an existing human strain picks up new genes from a virus that usually infects birds or pigs.

Influenza A, with its various subtypes (H3N2, H1N1, etc.) causes significant morbidity and mortality in humans and poses, for the foreseeable future, an significant threat of causing novel pandemics through genetic reassortments that can occur in other species such as birds and swine followed by transmission to humans.

Influenza A has been universally resistant to amantadine and rimantadine in recent years due to a mutation in the M2 proton channel drug target. The M2 protein is found in the viral envelope of influenza A virus and functions as a highly selective, pH-regulated proton channel important for the life cycle of the virus. Unlike neuraminidase inhibitors, rimantadine and amantadine are anti-viral agents capable of blocking the tetrameric M2 channel. In 2006, the U.S. Centers for Disease Control (CDC) issued an alert instructing clinicians to avoid using M2 ion-channel inhibitors during influenza season due to the extraordinarily high frequency of amantadine resistance in influenza A isolates associated with a single point mutation in the M2 protein, S31N. The drug-binding site is lined by residues that are mutated in amantadine-resistant viruses. Recently, it has been reported that resistance to rimantadine and amantadine in humans, birds and pigs has reached more than 90%, raising serious questions about the ability of these drugs alone to satisfy the need for treating influenza infections.

While some amantadine-like compounds have been found to be effective in vitro against influenza A, a persistent problem is the development of viral resistance to the potential therapeutic. Due to the propensity for M2 mutations, there has been very little investigation during the past 40 years into agents effective against the M2 target in influenza A. Since 2005, an amantadine- and rimantadine-insensitive S31N mutation has become highly prevalent in human influenza, abrogating clinical usefulness of amantadine and rimantadine. However, it has recently been recognized that the number of functional amantadine-insensitive M2 variations may be circumscribed to ~5. Previous attempts by others have failed to identify drugs active against the currently pervasive mutant, S31N.

Accordingly, there is a need to develop therapeutic agents for the treatment of influenza infections, particularly emerging mutant strains such as those in the different subtypes of influenza A, as well as combination products better suited to avoid resistance development.

SUMMARY

Compounds and pharmaceutically acceptable salts thereof are disclosed, including those of formulas I-III, VI, and VII. The compounds and their pharmaceutically acceptable salts may be used as antiviral compounds for preventing or treating amantadine-resistant forms of influenza A.

In compounds of formula I, $R^1$ is selected from $C_4$-$C_8$ alkyl, $C_1$-$C_5$ alkylenearyl, and aryl, wherein the aryl of alkylenearyl and aryl are optionally substituted with $C_1$-$C_4$ alkyl.

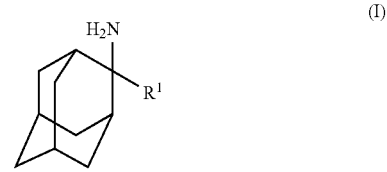

(I)

In compounds of formula II, $R^2$ is selected from H and methyl; and $R^3$ is selected from H, $C_1$-$C_4$ alkyleneamine, and $C_1$-$C_4$ alkyleneamino $C_1$-$C_4$ alkyl, and $C_1$-$C_4$ alkyleneamino di($C_1$-$C_4$ alkyl).

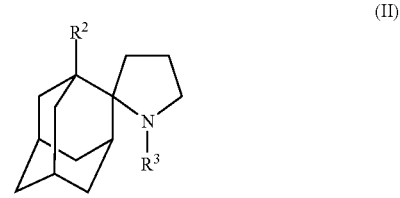

(II)

In compounds of formula III, each of $R^4$ and $R^5$ is independently selected from H and methyl.

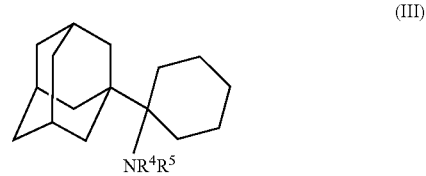

(III)

In compounds of formula VI, each of $R^{15}$ and $R^{16}$ is independently selected from $C_{1-8}$ alkyl.

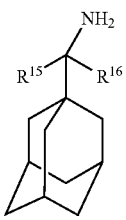

(VI)

In compounds of formula VII, each of $R^{17}$, $R^{18}$, $R^{19}$, and $R^{20}$ is independently selected from H and $C_{1-2}$ alkyl

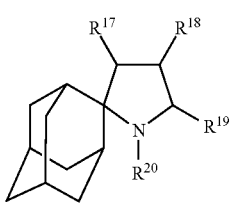

(VII)

Pharmaceutical compositions are also disclosed having a compound or a pharmaceutically acceptable salt thereof of any of formulas I-III, VI, and VII and a pharmaceutically acceptable carrier. In some embodiments, the pharmaceutical composition includes two or more compounds or pharmaceutically acceptable salts thereof of formula I-III and VI and a pharmaceutically acceptable carrier.

Methods of treating or preventing viral infections are disclosed, including administering to a patient in need thereof a compound or a pharmaceutically acceptable salt thereof of formulas I-III, VI, and VII or formulations containing the same with a pharmaceutically acceptable carrier. In some methods, the viral infection is influenza, such as influenza A including an influenza A infection having an amantadine-insensitive variation of M2, comprising administering to a patient in need thereof at least one compound or a pharmaceutically acceptable salt thereof of formulas I-III, formulas IV and V, formulas IVa, Va, VI, and VII.

In such methods with compounds of formula IV, $R^6$ is selected from hydrogen and methyl; $R^7$ and $R^8$ are independently selected from: hydrogen, phenyl, $C_1$-$C_8$ alkyl, OH, $NR^9R^{10}$, $C_1$-$C_5$ alkylenearyl, and aryl, wherein the aryl of alkylenearyl and aryl are optionally substituted with $C_1$-$C_4$ alkyl, or $R^7$ and $R^8$ together with the carbon atom to which they are attached form a 3-membered carbocyclic ring optionally substituted with NR'R", $C_1$-$C_4$ alkyleneamine, and $C_1$-$C_4$ alkyleneamino $C_1$-$C_4$ alkyl, and $C_1$-$C_4$ alkyleneamino di($C_1$-$C_4$ alkyl); wherein R' and R" are independently selected from hydrogen and $C_1$-$C_8$ alkyl; or $R^7$ and $R^8$ together with the carbon atom to which they are attached form a 5-, 6-, or 7-membered heterocyclic ring having from 1 to 3 nitrogen atoms, the ring optionally substituted with 1-3 substituents selected from oxo, OH, $C_1$-$C_8$ alkyl, $C_1$-$C_4$ alkyleneamine, $C_1$-$C_4$ alkyleneamino $C_1$-$C_4$ alkyl, and $C_1$-$C_4$ alkyleneamino di($C_1$-$C_4$ alkyl); provided that if $R^7$ and $R^8$ together with the carbon atom to which they are attached do not form a carbocyclic or heterocyclic ring, then one of $R^7$ and $R^8$ is OH or $NR^9R^{10}$; $R^9$ and $R^{10}$ are each independently selected from: hydrogen, $C_1$-$C_8$ alkyl, $C_1$-$C_4$ alkyleneamine, $C_1$-$C_4$ alkyleneamino $C_1$-$C_4$ alkyl, and $C_1$-$C_4$ alkyleneamino di($C_1$-$C_4$ alkyl).

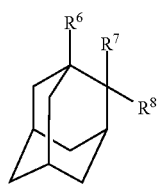

(IV)

In such methods with compounds of formula V, X is selected from hydrogen and halogen; $R^{11}$ is selected from: $NH_2$, a substituted or unsubstituted $C_3$-$C_8$ carbocyclic ring, and a substituted or unsubstituted 3-, 4-, 5-, 6-, or 7-membered heterocyclic ring having from 1 to 3 nitrogen atoms; wherein when the $C_3$-$C_8$ carbocyclic or 3-, 4-, 5-, 6-, or 7-membered heterocyclic rings are substituted, the substitution is selected from $C_1$-$C_8$ alkyl and $NR^{10}R^{11}$; wherein $R^{10}$ and $R^{11}$ are independently selected from hydrogen, $C_1$-$C_4$ alkyenelamine, $C_1$-$C_4$ alkyleneamino $C_1$-$C_4$ alkyl, and $C_1$-$C_4$ alkyleneamino di($C_1$-$C_4$ alkyl).

(V)

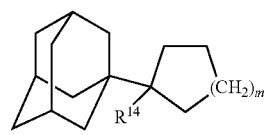

In such methods with compounds of formula IVa, $R^{12}$ is selected from hydrogen and methyl; $R^{13}$ is H, $C_1$-$C_8$ alkyl, or $C_1$-$C_8$ alkyleneamine; and n is an integer of from 1 to 2.

(IVa)

In such methods with compounds of formula Va, $R^{14}$ is selected from $NH_2$ and $NH(C_1$-$C_4$ alkyl) and m is an integer of from 1 to 2.

(Va)

DETAILED DESCRIPTION

The present invention may be understood more readily by reference to the following detailed description taken in connection with the accompanying examples, which form a part of this disclosure. It is to be understood that this disclosure is not limited to the specific products, methods, condition or parameters described and shown herein, and the terminology used herein is for the purpose of describing particularly embodiments by way of example only and is, therefore, not intended to be limiting of the claims.

While the terminology used in this application is standard within the art, the following definitions of certain terms are provided to assure clarity. Units, prefixes, and symbols may be denoted in their SI accepted form. Numeric ranges recited herein are inclusive of the numbers defining the range and include and are supportive of each integer within the defined range. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The term "alkyl" refers to a branched or straight-chained hydrocarbon radical (group) having at least one carbon atom including, but not limited to $C_1$-$C_4$ such as: methyl, ethyl, 1-propyl and 2-propyl, 1-butyl, 2-butyl, 2-methyl-1-propyl, 1,1-dimethyl-ethyl; $C_5$-$C_6$ such as: 1-pentyl, 2-pentyl, 3-pentyl, 2-methyl-1-butyl, 3-methyl-1-butyl, 2,2-dimethyl-propyl, 1-hexyl, 2-hexyl, 3-hexyl, 2-methyl-1-pentyl, 3-methyl-1-pentyl, 4-methyl-1-pentyl, 3,3-dimethyl-1-butyl, 3,3-dimethyl-2-butyl, 2-ethyl-1-butyl and the like.

The term "alkylene" refers to a divalent alkyl moiety, meaning the alkylene moiety is attached to the rest of the molecule at both ends of the alkyl unit. Thus, alkyleneamine represents an alkyl radical linked to a molecule while the other end of the alkyl radical is linked to an amine group ($NH_2$). The terms "alkyleneamino alkyl" and "alkyleneamino dialkyl" represent an alkyl radical linked to a molecule while the other end of the alkyl radical is linked to an amino nitrogen atom which is substituted with an alkyl group or two alkyl groups in the case of dialkyl.

The term "alkylenearyl" refers to a divalent alkyl group linked to a molecule and on the other end of the alkyl unit is linked to an aryl group such as a phenyl.

As used herein, "aryl" refers to an aromatic group which has at least one ring having a conjugated π electron system and includes carbocyclic aryl, heterocyclic aryl and biaryl groups. The aryl group may be optionally substituted with one or more substituents including halogen, trihalomethyl, hydroxyl, SH, OH, $NO_2$, $NH_2$, thioether, cyano, alkoxy, alkyl, and amino. Examples of carbocyclic aryl include phenyl, naphthyl, biphenylenyl, penta-2,4-diene, anthracenyl, azulenyl, indacenyl, and the like.

The term "carbocyclyl" refers to a saturated ring having only carbon atoms (no heteroatoms). Examples include cyclopentyl, cyclohexyl, cycloheptyl, cyclooctyl, or saturated bicyclic ring, such as a "monocycle" (like those above) that is fused with a saturated ring moiety of 5 to 8 ring atoms, e.g. with a cyclohexyl moiety.

As used herein, "heterocycle" or "heterocyclic ring" refers to a ring system having one to three nitrogen heteroatoms (N) as part of the ring in place of one or more carbon atoms. Examples or heterocyclic groups include but are not limited to piperidyl, morpholinyl, pyranyl, dioxanyl, and piperazinyl. The hetrocyclic ring may be substituted or unsubstituted. Examples of substitution groups include alkyl, amino, alkylamino, and dialkylamino.

The term "fused" when used with aryl or heterocycle refers to the aryl or heterocyclyl group sharing a common bond with another cyclic group such as a phenyl.

The terms "hydroxyl" and "hydroxy" both refer to an OH group.

As used herein, the terms "treatment" or "therapy" (as well as different word forms thereof) includes preventative (e.g., prophylactic), curative or palliative treatment.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The disclosed compounds may be prepared in the form of pharmaceutically acceptable salts. "Pharmaceutically acceptable salts" refer to derivatives of the disclosed compounds wherein the parent compound is modified by making acid salts thereof. Examples of pharmaceutically acceptable salts include, but are not limited to, mineral or organic acid salts of basic residues such as amines; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol.

Viral infections can be treated with antiviral compounds. For example, viral infections include those brought about by influenza A, influenza B, and influenza C. Among the various forms of influenza A, B, and C, there are subtypes of each, particularly among influenza A.

One vulnerability of influenza A is blockage of the few M2 proton channels in its envelope, which are required by the virus for acidification of the virus interior and alkalinization of the trans-Golgi network during cell infection. Amantadine and rimantadine block proton transport in the wild type influenza A M2, and are effective prophylactics and therapeutics against influenza A.

While some derivatives of amantadine have been investigated and found effective in vitro against influenza A, resistance to amantadine develops rapidly in the clinical setting through mutations at residues 26, 27, 30, 31, or 34 whose side chains are near the 4-fold symmetric binding site. Since about 2005, the amantadine- and rimantadine-insensitive S31N mutation has become highly prevalent in human infectious forms of influenza, abrogating clinical usefulness of amantadine and rimantadine.

Figure 1:
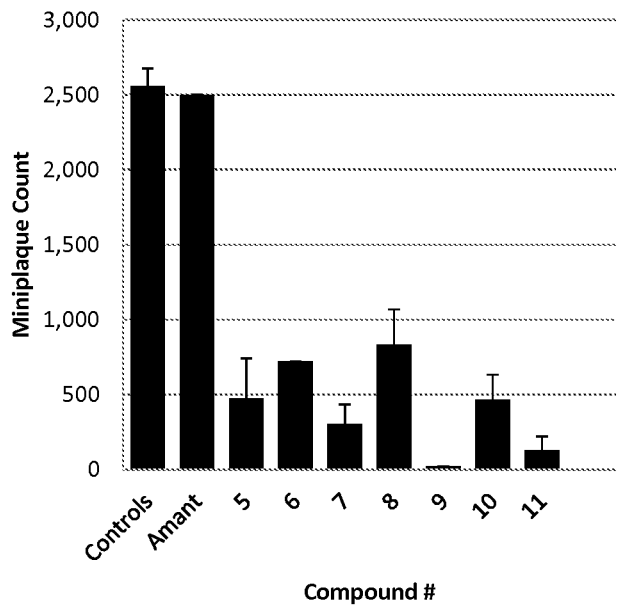
FIG. 1A shows H1N1 infections of MDCK cells with compounds from Scheme A. Screening was performed using 100 μM drug in the culture medium. Error bars, where present represent the standard deviation for the two replicas, otherwise N=1.
FIG. 1B shows the results of a dose-response study for compound 7 from Scheme A. Error bars are ±1 S.D.
Figure 1:
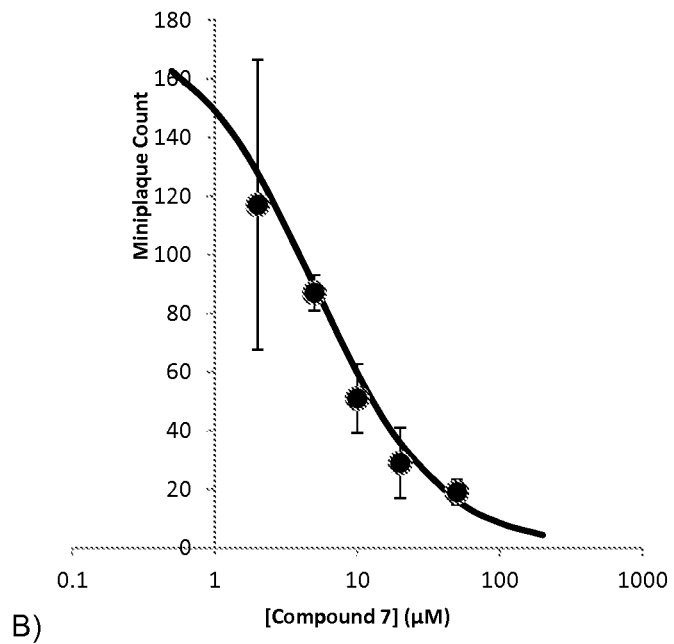
Figure 2:
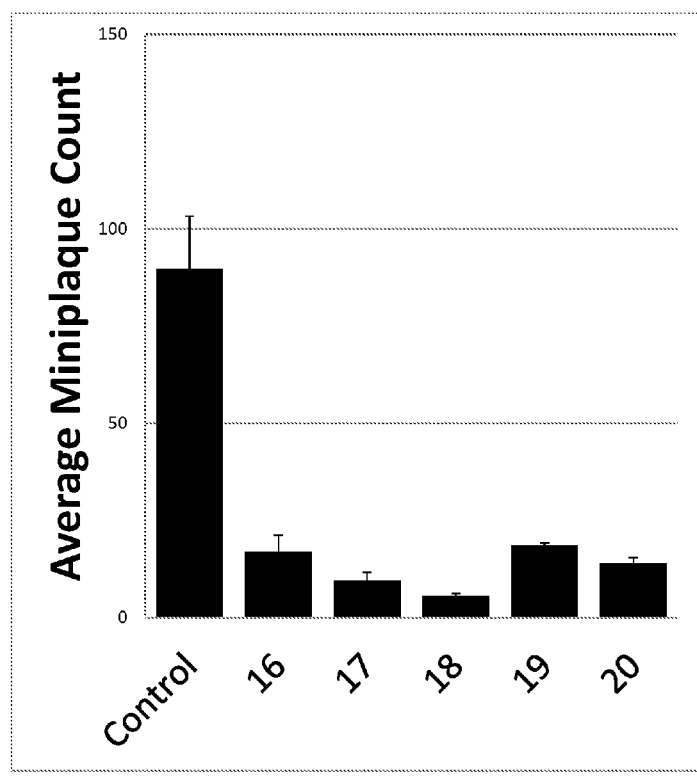
FIG. 2 shows anti-H1N1 screen results for compounds in Scheme B with drug concentrations at 50 μM. N=4 (drug-free control) or N=2 (with drug).

The M2 proton channel is a 4-fold symmetric, homotetrameric, 4-trans-membrane helix bundle that exchanges protons for alkali metal cations across the envelope or trans-Golgi membrane, taking advantage of selectivity for protons conferred by the four His37 imidazoles at the core of the transport function to counterbalance a huge concentration advantage enjoyed by the alkali metal cations, which would otherwise competitively inhibit proton uptake.

The primary drug target domain binding site is the lumen of a four-helix bundle that forms the proton transport path. The N-terminal entryway to the binding site is lined by Val27 side chains and the C-terminal (intraviral) exit is blocked by His37 and Trp41 side chains.

Novel amantadine derivatives are disclosed herein that are potent and persistent inhibitors of Influenza A/California/07/2009 (H1N1), which bears the S31N mutation. Other amantadine derivatives, which have been investigated and found, in some cases, to be active against the wild type (S31-bearing) M2, have also been discovered to be effective, both potent and persistent, against the S31N-bearing 2009 H1N1 strain of influenza A.

Adamantane compounds block influenza A virus strains in idiosyncratic ways, blocking some strains better than others. Substrains of influenza A that contain wild type (WT) residues in the internal amantadine binding site of the M2 channel are generally blocked by amantadine, but may vary in efficacy. In some cases, WT H1N1 and H2N2 substrains have been shown to be sensitive to adamantane compounds where WT H3N2 were less sensitive. It has also been shown that substrains with mutations in the internal amantadine binding site (i.e. at amino acid numbers 26, 27, 30, 31, and 34) are generally not blocked by amantadine. Although some in the art have predicted that the most common of these mutations, S31N, is so minor that it has little effect on the protein size or drug binding efficacy for adamantane analogs like those disclosed here, this has been found not to be the case in experimental assays. Of many drugs tested by many in the art, virtually all that block influenza A with WT M2 do not block the S31N M2 variant, whether it be the H1N1, H2N2, or H3N2 influenza A substrain. Adamantane compounds have not yet been tested against the more deadly influenza A substrains, H5N1 and H7N9, but would be expected by those working in the art to block those containing WT M2 but not those with S31N M2.

Thus, there are over 12,000 genetic sequences for different isolates of influenza A in the current databases, most of which differ in some way from all others. Some compounds can block some S31N M2 bearing isolates of H1N1 and not others. In the present disclosure, identified drugs can block cell culture infections by the virus even though it does not block the M2 channel itself in direct testing (i.e. electrophysiology).

Thus alternative mechanisms exist by which the adamantanamines disclosed herein might block infection. Without wishing to be bound to any one theory, amino compounds might buffer the endosome, leading to failure of acidification and thus viral fusion. This behavior might be expected to differ from one compound to another based on their membrane permeability and the availability of the neutral titration state of the drug. Many other as-yet unconsidered mechanisms may also be important. For instance, those in the art believe that M2 is important for viral replication because it specifically allows acid to enter the virus and titrate ribonuclear proteins, which is necessary for their release from the capsid. Perhaps as in the endosome buffering theory, the adamantanamines disclosed herein buffer the viral interior and prevent acidification. The same permeability parameters would affect efficacy. These small, amphiphilic compounds are known to bind to the interface of lipid membranes. They may alter the mechanical properties of the membrane and inhibit fusion of the viral envelope with the endosome membrane, blocking ribonuclear protein release into the cytoplasm of the cell. There may be other proteins in the virus and infected cell that are important to viral infection, which may be bound up by these compounds and inhibited. For instance, hemagglutinin must undergo a conformational change to induce fusion of the viral envelope with the endosome membrane, and compounds similar in size to the adamantanamines, such as tert-butyl hydroquinone, are known to bind to hemagglutinin and prevent its change to the fusigenic conformation. Regardless of the mechanism or biological pathway for efficacy, the drugs presented herein show unexpected efficacy in cell culture assays for certain amantadine-insensitive isolates such as the pandemic 2009 H1N1. Even more unexpected in the art is that compounds representative of both the prior art set disclosed and the novel composition set were persistent in their effectiveness against one such isolate, A/California/07/2009, i.e. were highly invulnerable to the development of viral resistance.

In one aspect, compounds for treating viral infections are disclosed. The compounds include those of formula I and pharmaceutically acceptable salts thereof.

$$\text{(I)}$$

[Structure: adamantane with H$_2$N and R$^1$ substituents at the 2-position]

In formula I, R$^1$ is selected from C$_4$-C$_8$ alkyl, C$_1$-C$_5$ alkylenearyl, and aryl. The aryl of alkylenearyl and aryl may optionally substituted with C$_1$-C$_4$ alkyl. In some embodiments, R$^1$ is C$_4$-C$_8$ alkyl. In some embodiments, R$^1$ is branched C$_4$-C$_8$ alkyl such as iso-butyl, sec-butyl, tert-butyl, n-pentyl, —CH$_2$C(CH$_3$), and the like. In some embodiments, R$^1$ is straight C$_4$-C$_8$ alkyl such as n-butyl, n-pentyl, n-hexyl, n-heptyl, and n-octyl.

In some embodiments, R$^1$ is C$_5$-C$_8$ alkyl. In some embodiments, R$^1$ is C$_6$-C$_8$ alkyl.

In some embodiments, R$^1$ is C$_1$-C$_5$ alkylenearyl wherein the aryl of alkylenearyl is optionally substituted with C$_1$-C$_4$ alkyl.

In some embodiments, R$^1$ is aryl is optionally substituted with C$_1$-C$_4$ alkyl. In some embodiments, R$^1$ is aryl is optionally substituted with methyl. The methyl substitution may be o-, m-, or p-substituted. In some embodiments, R$^1$ is unsubstituted benzyl. In some embodiments, R$^1$ is unsubstituted phenyl.

In some embodiments, the compounds of Formula I exclude compounds where R$^1$ is n-butyl ((1r,3r,5r,7r)-2-butyladamantan-2-amine). In some embodiments, the compounds of Formula I exclude compounds where R$^1$ is n-pentyl (1r,3r,5r,7r)-2-pentyladamantan-2-amine. In some embodiments, the compounds of Formula I exclude compounds where R$^1$ is phenyl ((1r,3r,5r,7r)-2-phenyladamantan-2-amine).

In another aspect, compounds for treating viral infections include those of formula II and pharmaceutically acceptable salts thereof.

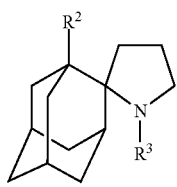

(II)

In formula II, $R^2$ is selected from H and methyl; $R^3$ is selected from H, $C_1$-$C_4$ alkylene-amine, and $C_1$-$C_4$ alkyleneamino $C_1$-$C_4$ alkyl, and $C_1$-$C_4$ alkyleneamino di($C_1$-$C_4$ alkyl).

In some embodiments, $R^2$ is methyl and $R^3$ is H. In some embodiments, $R^2$ is H. In some embodiments, $R^3$ is $C_1$-$C_4$ alkyleneamine such as ethylamine.

In some embodiments, compounds of Formula II exclude compounds where $R^2$ is H and $R^3$ is H namely (1r,3r,5r,7r)-spiro[adamantane-2,2'-pyrrolidine]. In some embodiments, the compounds of Formula II exclude compounds where $R^2$ is H and $R^3$ is $CH_2NH_2$, namely ((1r,3r,5r,7r)-spiro[adamantane-2,2'-pyrrolidin]-1'-yl)methanamine. In some embodiments, compounds of Formula II exclude compounds where $R^2$ is H and $R^3$ is $CH_2NH_2$, namely 2-((1r,3r,5r,7r)-spiro[adamantane-2,2'-pyrrolidin]-1'-yl)ethan-1-amine.

In another aspect, compounds for treating viral infections include those of formula III and pharmaceutically acceptable salts thereof.

(III)

In formula III, each of $R^4$ and $R^5$ is independently selected from H and methyl. In some embodiments, $R^4$ and $R^5$ are both H. In some embodiments, $R^4$ and $R^5$ are both $CH_3$. In some embodiments, $R^4$ is H and $R^5$ is $CH_3$.

In another aspect, compounds for treating viral infections include those of formula VI and pharmaceutically acceptable salts thereof.

(VI)

In formula VI, each of $R^{15}$ and $R^{16}$ is independently selected from $C_{1-8}$ alkyl. In some embodiments, $R^{15}$ is selected from $C_{1-6}$ alkyl. In some embodiments, $R^{15}$ is selected from $C_{1-3}$ alkyl. In some embodiments, $R^{15}$ is methyl. In some embodiments, $R^{15}$ is ethyl. In some embodiments, $R^{15}$ is propyl. In some embodiments, $R^{16}$ is selected from $C_{1-6}$ alkyl. In some embodiments, $R^{16}$ is selected from $C_{1-3}$ alkyl. In some embodiments, $R^{16}$ is methyl. In some embodiments, $R^{16}$ is ethyl. In some embodiments, $R^{16}$ is propyl. In some embodiments, each of $R^{15}$ and $R^{16}$ are the same. In some embodiments, each of $R^{15}$ and $R^{16}$ are different.

In another aspect, compounds for treating viral infections include those of formula VII and pharmaceutically acceptable salts thereof.

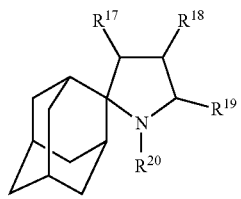

(VII)

In formula VII, each of $R^{17}$, $R^{18}$, $R^{19}$, and $R^{20}$ is independently selected from H and $C_{1-2}$ alkyl. In some embodiments, one of $R^{17}$, $R^{18}$, and $R^{19}$ is $C_{1-2}$ alkyl and the others are H. In some embodiments, $R^{17}$ is $CH_3$ and $R^{18}$ and $R^{19}$ are H. In some embodiments, $R^{18}$ is $CH_3$ and $R^{17}$ and $R^{19}$ are H. In some embodiments, $R^{19}$ is $CH_3$ and $R^{17}$ and $R^{18}$ are H. In some embodiments, $R^{19}$ is $CH_2CH_3$ and $R^{17}$ and $R^{18}$ are H. In some embodiments, $R^{20}$ is H. In some embodiments, $R^{20}$ is $C_{1-2}$ alkyl. In some embodiments, $R^{20}$ is $CH_3$. In some embodiments, $R^{20}$ is $CH_2CH_3$. In some embodiments, $R^{20}$ is H.

In one aspect, a pharmaceutical composition includes a compound or a pharmaceutically acceptable salt thereof of formulas I-III and a pharmaceutically acceptable carrier is disclosed. In another aspect, a pharmaceutical composition includes two or more compounds or pharmaceutically acceptable salts thereof of formulas I-III and a pharmaceutically acceptable carrier is disclosed.

In one aspect, a pharmaceutical composition includes a compound or a pharmaceutically acceptable salt thereof of formulas I-III, VI, and VII and a pharmaceutically acceptable carrier is disclosed. In another aspect, a pharmaceutical composition includes two or more compounds or pharmaceutically acceptable salts thereof of formulas I-III, VI, and VII and a pharmaceutically acceptable carrier is disclosed.

In another aspect, a method of treating or preventing a viral infection, includes administering to a patient in need thereof a compound or a pharmaceutically acceptable salt thereof using a compound of formulas I-III or a composition including a compound of formulas I-III and a pharmaceutically acceptable carrier. In some embodiments, the viral infection is influenza. In some embodiments, the viral infection is influenza A. In some embodiments, the viral infection is influenza A infection having an amantadine-insensitive variation of M2.

In another aspect, a method of treating or preventing an influenza A infection having an amantadine-insensitive variation of M2 includes administering to a patient in need thereof at least one compound or a pharmaceutically acceptable salt thereof of formula IV or V.

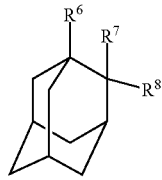

(IV)

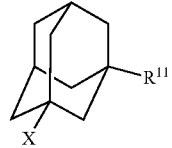

(V)

In formula IV, $R^6$ is selected from hydrogen and methyl; $R^7$ and $R^8$ are independently selected from: hydrogen, phenyl, $C_1$-$C_8$ alkyl, OH, $NR^9R^{10}$, $C_1$-$C_5$ alkylenearyl, and aryl, wherein the aryl of alkylenearyl and aryl are optionally substituted with $C_1$-$C_4$ alkyl, or $R^7$ and $R^8$ together with the carbon atom to which they are attached form a 3-membered carbocyclic ring optionally substituted with NR'R", $C_1$-$C_4$ alkyleneamine, and $C_1$-$C_4$ alkyleneamino $C_1$-$C_4$ alkyl, and $C_1$-$C_4$ alkyleneamino di($C_1$-$C_4$ alkyl); wherein R' and R" are independently selected from hydrogen and $C_1$-$C_8$ alkyl; or $R^7$ and $R^8$ together with the carbon atom to which they are attached form a 5-, 6-, or 7-membered heterocyclic ring having from 1 to 3 nitrogen atoms, the ring optionally substituted with 1-3 substituents selected from oxo, OH, $C_1$-$C_8$ alkyl, $C_1$-$C_4$ alkyleneamine, $C_1$-$C_4$ alkyleneamino $C_1$-$C_4$ alkyl, and $C_1$-$C_4$ alkyleneamino di($C_1$-$C_4$ alkyl); provided that if $R^7$ and $R^8$ together with the carbon atom to which they are attached do not form a carbocyclic or heterocyclic ring, then one of $R^7$ and $R^8$ is OH or $NR^9R^{10}$; $R^9$ and $R^{10}$ are each independently selected from: hydrogen, $C_1$-$C_8$ alkyl, $C_1$-$C_4$ alkyleneamine, $C_1$-$C_4$ alkyleneamino $C_1$-$C_4$ alkyl, and $C_1$-$C_4$ alkyleneamino di($C_1$-$C_4$ alkyl).

In formula V, X is selected from hydrogen and halogen; $R^{11}$ is selected from: $NH_2$, a substituted or unsubstituted $C_3$-$C_8$ carbocyclic ring, and a substituted or unsubstituted 3-, 4-, 5-, 6-, or 7-membered heterocyclic ring having from 1 to 3 nitrogen atoms; wherein when the $C_3$-$C_8$ carbocyclic or 3-, 4-, 5-, 6-, or 7-membered heterocyclic rings are substituted, the substitution is selected from $C_1$-$C_8$ alkyl and $NR^{10}R^{11}$; wherein $R^{10}$ and $R^{11}$ are independently selected from hydrogen, $C_1$-$C_4$ alkyenelamine, $C_1$-$C_4$ alkyleneamino $C_1$-$C_4$ alkyl, and $C_1$-$C_4$ alkyleneamino di($C_1$-$C_4$ alkyl).

In some embodiments, $R^6$ is methyl. In some embodiments, $R^7$ and $R^8$ together with the carbon atom to which they are attached form a 5-membered heterocyclic ring having 1 nitrogen atom.

In some embodiments, $R^6$ is hydrogen. In some embodiments, $R^7$ and $R^8$ together with the carbon atom to which they are attached form a 3-membered carbocyclic ring optionally substituted with NR'R" and $C_1$-$C_4$ alkyleneamine, wherein R' and R" are independently selected from hydrogen and $C_1$-$C_4$ alkyl. In some embodiments, the carbocyclic ring is substituted with NR'R" and R' and R" are both hydrogen. In some embodiments, the carbocyclic ring is substituted with $(CH_2)NH_2$. In some embodiments, $R^8$ is selected from $NH_2$ and OH. In some embodiments, $R^8$ is $NH_2$. In some embodiments, $R^8$ is OH. In some embodiments, $R^7$ is methyl. In some embodiments, $R^7$ is n-propyl. In some embodiments, $R^7$ is n-propyl. In some embodiments, $R^7$ is H.

In some embodiments, $R^7$ and $R^8$ together with the carbon atom to which they are attached form a 5- or 6-membered heterocyclic ring having one nitrogen atom optionally substituted with oxo, $C_1$-$C_8$ alkyl, $C_1$-$C_4$ alkyleneamine. In some embodiments, the heterocyclic ring has 5 members. In some embodiments, the heterocyclic ring is substituted with oxo. In some embodiments, the heterocyclic nitrogen is unsubstituted. In some embodiments, heterocyclic nitrogen is substituted with methyl. In some embodiments, the heterocyclic ring is substituted with ethylamine. In some embodiments, the heterocyclic ring has 6 members and is unsubstituted.

In some embodiments, $R^7$ is $NH_2$. In some embodiments, $R^8$ is $C_1$-$C_8$ alkyl. In some embodiments, $R^8$ is ethyl. In some embodiments, $R^8$ is $C_4$-$C_8$ alkyl. In some embodiments, $R^8$ is n-butyl. In some embodiments, $R^8$ is iso-butyl. In some embodiments, $R^8$ is phenyl. In some embodiments, $R^8$ is benzyl.

In some embodiments, $R^8$ is $NH_2$. In some embodiments, $R^7$ is $C_1$-$C_8$ alkyl. In some embodiments, $R^7$ is ethyl. In some embodiments, $R^7$ is $C_4$-$C_8$ alkyl. In some embodiments, $R^7$ is n-butyl. In some embodiments, $R^7$ is iso-butyl. In some embodiments, $R^8$ is phenyl. In some embodiments, $R^7$ is benzyl.

In some embodiments of formula V, X is fluoro and $R^{11}$ is $NH_2$. In some embodiments, X is hydrogen. In some embodiments, $R^{11}$ is a substituted $C_5$-$C_6$ carbocyclic ring. In some embodiments, the carbocyclic ring has 5 members and is substituted with $NH_2$. In some embodiments, the carbocyclic ring has 6 members and is substituted with $NH_2$. In some embodiments, $R^{11}$ is 5-membered, unsubstituted heterocyclic ring having 1 nitrogen atom. In some embodiments, $R^{11}$ is 6-membered, unsubstituted heterocyclic ring having 1 nitrogen atom.

In some embodiments, compounds of Formula IV exclude compounds where $R^6$ is H. In some embodiments, compounds of Formula IV exclude compounds where $R^7$ and $R^8$ form a pyrolidin-2-yl or piperidin-2-yl ring.

In some embodiments, compounds of Formula IV exclude compounds where $R^6$ is H, and $R^7$ and $R^8$ form a pyrolidin-2-yl ring, namely (1r,3r,5r,7r)-spiro[adamantane-2,2'-pyrrolidine]. In some embodiments, compounds of Formula IV exclude compounds where $R^6$ is H, and $R^7$ and $R^8$ form a piperdin-2-yl ring, namely (1r,3r,5r,7r)-spiro[adamantane-2,2'-piperidine]. In some embodiments, compounds of Formula IV exclude compounds where $R^6$ is H, and $R^7$ and $R^8$ form a 1-methylpyrolidin-2-yl ring, namely (1r,3r,5r,7r)-1'-methylspiro[adamantane-2,2'-pyrrolidine]. In some embodiments, compounds of Formula IV exclude compounds where $R^6$ is H, and $R^7$ and $R^8$ form a 1-methyl-piperidin-2-yl ring, namely (1r,3r,5r,7r)-1'-methylspiro[adamantane-2,2'-piperidine]. In some embodiments, compounds of Formula IV exclude compounds where $R^6$ is H, and $R^7$ and $R^8$ form a 1-ethyl-pyrolidin-2-yl ring, namely (1r,3r,5r,7r)-1'-ethyl-spiro[adamantane-2,2'-pyrrolidine]. In some embodiments, compounds of Formula IV exclude compounds where $R^6$ is H, and $R^7$ and $R^8$ form a 1-ethyl-piperidin-2-yl ring, namely (1r,3r,5r,7r)-1'-ethylspiro[adamantane-2,2'-piperidine]. In some embodiments, compounds of Formula IV exclude compounds where $R^6$ is H, and $R^7$ and $R^8$ form a 1-methyleneamino-pyrolidin-2-yl ring, namely ((1r,3r,5r,7r)-spiro[adamantane-2,2'-pyrrolidin]-1'-yl)methanamine.

In some embodiments, compounds of Formula IV exclude compounds where $R^7$ is OH. In some embodiments, compounds of Formula IV exclude compounds where $R^7$ is OH and $R^8$ is $C_{1-3}$ alkyl. In some embodiments, compounds of Formula IV exclude compounds where $R^7$ is OH and $R^8$ is $C_{1-4}$ alkyl.

In some embodiments, compounds of Formula IV exclude compounds where $R^6$ is H, $R^7$ is OH, and $R^8$ is methyl, namely (1r,3r,5r,7r)-2-methyladamantan-2-ol. In some embodiments, compounds of Formula IV exclude compounds where $R^6$ is H, $R^7$ is OH, and $R^8$ is ethyl, namely (1r,3r,5r,7r)-2-ethyladamantan-2-ol. In some embodiments, compounds of Formula IV exclude compounds where $R^6$ is H, $R^7$ is OH, and $R^8$ is propyl, namely (1r,3r,5r,7r)-2-propyladamantan-2-ol.

In some embodiments, compounds of Formula IV exclude compounds where $R^8$ is pyridine-2-yl. In some embodiments, compounds of Formula IV exclude compounds where $R^8$ is pyrimidin-1-yl. In some embodiments, compounds of Formula IV exclude compounds where $R^8$ is azairidin-2-yl. In some embodiments, compounds of Formula IV exclude compounds where $R^8$ is piperidin-2-yl. In some embodiments, compounds of Formula IV exclude compounds where $R^8$ is piperidin-3-yl. In some embodiments, compounds of Formula IV exclude compounds where $R^8$ is morpholin-3-yl. In some embodiments, compounds of Formula IV exclude compounds where $R^8$ is pyrrolidin-2-yl. In some embodiments, compounds of Formula IV exclude compounds where $R^8$ is pyrrolidin-3-yl.

In some embodiments, compounds of Formula IV exclude compounds where $R^6$ is H, $R^7$ is methylamino, and $R^8$ is pyridine-2-yl, namely (1r,3r,5r,7r)-N-methyl-2-(pyridin-2-yl)adamantan-2-amine.

In some embodiments, compounds of Formula IV exclude compounds where $R^6$ is H, and $R^7$ and $R^8$ form a 2,5-pyrimidin-1-yl-2',4',6'(1'H,3'H)-trione ring, namely (1r,3r,5r,7r)-2'H-spiro[adamantane-2,5'-pyrimidine]-2',4',6'(1'H,3'H)-trione. In some embodiments, compounds of Formula IV exclude compounds where $R^6$ is H, and $R^7$ and $R^8$ form a 1-methyl-aziridin-2-yl ring, namely (1r,3r,5r,7r)-1'-methylspiro[adamantane-2,2'-aziridine]. In some embodiments, compounds of Formula IV exclude compounds where $R^6$ is H, and $R^7$ and $R^8$ form a 1-methyl-aziridin-2-yl ring, namely (1r,3r,5r,7r)-1'-methylspiro[adamantane-2,2'-azetidine]. In some embodiments, compounds of Formula IV exclude compounds where $R^6$ is H, and $R^7$ and $R^8$ form a piperidin-3-yl-6-one ring, namely (1r,3r,5r,7r)-spiro[adamantane-2,3'-piperidin]-6'-one. In some embodiments, compounds of Formula IV exclude compounds where $R^6$ is H, and $R^7$ and $R^8$ form a 1-methylpiperidin-2-yl ring, namely (1r,3r,5r,7r)-1'-methylspiro[adamantane-2,2'-piperidine]. In some embodiments, compounds of Formula IV exclude compounds where $R^6$ is H, and $R^7$ and $R^8$ form a 1-ethylpiperidin-2-yl ring, namely (1r,3r,5r,7r)-1'-ethylspiro[adamantane-2,2'-piperidine].

In some embodiments, compounds of Formula IV exclude compounds where $R^6$ is H, and $R^7$ and $R^8$ form a morpholin-3-yl ring, namely (1r,3r,5r,7r)-spiro[adamantane-2,3'-morpholine]. In some embodiments, compounds of Formula IV exclude compounds where $R^6$ is H, and $R^7$ and $R^8$ form a 4-methylmorpholin-3-yl ring, namely (1r,3r,5r,7r)-4'-methylspiro[adamantane-2,3'-morpholine]. In some embodiments, compounds of Formula IV exclude compounds where $R^6$ is H, and $R^7$ and $R^8$ form an 4-ethylmorpholin-3-yl ring, namely (1r,3r,5r,7r)-4'-ethylspiro[adamantane-2,3'-morpholine]. In some embodiments, compounds of Formula IV exclude compounds where $R^6$ is H, and $R^7$ and $R^8$ form a morpholin-3-yl-5-one ring, namely, (1r,3r,5r,7r)-spiro[adamantane-2,3'-morpholin]-5'-one.

In some embodiments, compounds of Formula IV exclude compounds where $R^6$ is H, and $R^7$ and $R^8$ form a 1-methylpyrrolidin-3-yl ring, namely, (1r,3r,5r,7r)-1'-methylspiro[adamantane-2,2'-pyrrolidine]. In some embodiments, compounds of Formula IV exclude compounds where $R^6$ is H, and $R^7$ and $R^8$ form a 1-ethylpyrrolidin-3-yl ring, namely, (1r,3r,5r,7r)-1'-ethylspiro[adamantane-2,2'-pyrrolidine]. In some embodiments, compounds of Formula IV exclude compounds where $R^6$ is H, and $R^7$ and $R^8$ form a pyrrolidin-2-yl-5-one ring, namely, (1r,3r,5r,7r)-spiro[adamantane-2,2'-pyrrolidin]-5'-one.

In some embodiments, compounds of Formula V exclude compounds where X is H and $R^{11}$ is 1-amino-cyclopentan-1-yl, namely 1-((1r,3r,5r,7r)-adamantan-2-yl)cyclopentan-1-amine. In some embodiments, compounds of Formula V exclude compounds where X is H and $R^{11}$ is 1-N-methyl-amino-cyclopentan-1-yl, namely 1-((1r,3r,5r,7r)-adamantan-2-yl)-N-methylcyclopentan-1-amine.

In some embodiments, compounds of Formula V exclude compounds where X is F and $R^{11}$ is amino, namely (1r,3s,5R,7S)-3-fluoroadamantan-1-amine. In some embodiments, compounds of Formula V exclude compounds where X is Cl and $R^{11}$ is amino, namely (1 r,3s,5R,7S)-3-chloroadamantan-1-amine. In some embodiments, compounds of Formula V exclude compounds where X is Br and $R^{11}$ is amino, namely (1 r,3s,5R,7S)-3-bromoadamantan-1-amine. In some embodiments, compounds of Formula V exclude compounds where X is H and $R^{11}$ is amino, namely (3s,5s,7s)-adamantan-1-amine.

In some embodiments, compounds of Formula V exclude compounds where X is H and $R^{11}$ is cyclopentyl, namely (3r,5r,7r)-1-cyclopentyladamantane. In some embodiments, compounds of Formula V exclude compounds where X is H and $R^{11}$ is cyclooctyl, namely (3r,5r,7r)-1-cyclooctyladamantane.

In some embodiments, compounds of Formula V exclude compounds where X is H and $R^{11}$ is aziridin-1-yl, namely 1-((3s,5s,7s)-adamantan-1-yl)aziridine. In some embodiments, compounds of Formula V exclude compounds where X is H and $R^{11}$ is aziridin-2-yl, namely 2-((3r,5r,7r)-adamantan-1-yl)aziridine. In some embodiments, compounds of Formula V exclude compounds where X is H and $R^{11}$ is azetidin-1-yl, namely 1-((3s,5s,7s)-adamantan-1-yl)azetidine. In some embodiments, compounds of Formula V exclude compounds where X is H and $R^{11}$ is azetidin-2-yl, namely 2-((3r,5r,7r)-adamantan-1-yl)azetidine. In some embodiments, compounds of Formula V exclude compounds where X is H and $R^{11}$ is pyrrolidin-1-yl, namely 1-((3s,5s,7s)-adamantan-1-yl)pyrrolidine. In some embodiments, compounds of Formula V exclude compounds where X is H and $R^{11}$ is pyrrolidin-2-yl, namely 2-((3r,5r,7r)-adamantan-1-yl)pyrrolidine. In some embodiments, compounds of Formula V exclude compounds where X is H and $R^{11}$ is piperidin-2-yl, namely 2-((3r,5r,7r)-adamantan-1-yl)piperidine. In some embodiments, compounds of Formula V exclude compounds where X is H and $R^{11}$ is azepan-1-yl, namely 1-((3s,5s,7s)-adamantan-1-yl)azepane. In some embodiments, compounds of Formula V exclude compounds where X is H and $R^{11}$ is azepan-2-yl, namely 2-((3r,5r,7r)-adamantan-1-yl)azepane.

In another aspect, a method for treating or preventing influenza A infection, includes administering to a patient in need thereof a compound or a pharmaceutically acceptable salt thereof of formula IVa or Va:

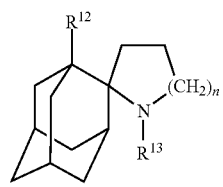

(IVa)

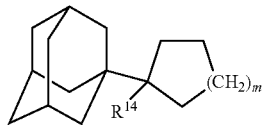

(Va)

In compounds of formula IVa, $R^{12}$ is selected from hydrogen and methyl; $R^{13}$ is H, $C_1$-$C_8$ alkyl, or $C_1$-$C_8$ alkyleneamine; n is an integer of from 1 to 2.

In compounds of formula Va, $R^{14}$ is selected from $NH_2$ and $NH(C_1$-$C_4$ alkyl); m is an integer of from 1 to 2.

In one aspect, the method of treating or preventing an influenza A infection having an amantadine-insensitive variation of M2 includes administering to a patient in need thereof at least two or more compounds or pharmaceutically acceptable salts thereof of formulas IV, V, IVa, and Va. In some embodiments, the infection is influenza A having an S31N amantadine-insensitive variant of M2.

Formulations and Routes of Administration

The compounds described herein, or pharmaceutically acceptable addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

The active compound(s) may be administered per se or in the form of a pharmaceutical composition wherein the active compound(s) is in admixture with one or more pharmaceutically acceptable carriers, excipients or diluents. Pharmaceutical compositions for use with the compounds described above may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee (tablet) cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant (such as dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

The compounds may be formulated for parenteral administration by injection (such as by bolus injection or continuous infusion). Formulations for injection may be presented in unit dosage form (in ampoules or in multi-dose containers) with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension (such as sodium carboxymethyl cellulose, sorbitol, or dextran). Optionally, the suspension may also contain suitable stabilizers or agents which increase the solubility of the compounds to allow for the preparation of highly concentrated solutions. Alternatively, the active ingredient may be in powder form for constitution with a suitable vehicle (such as sterile pyrogen-free water) before use. The compounds may also be formulated in rectal compositions such as suppositories or retention enemas (such as containing conventional suppository bases like cocoa butter or other glycerides).

In addition to the formulations described previously, the compounds may also be formulated as a depot preparation. Such long acting formulations may be administered by implantation or transcutaneous delivery (such as subcutaneously or intramuscularly), intramuscular injection or a transdermal patch. Thus, the compounds may be formulated with suitable polymeric or hydrophobic materials (such as an emulsion in an acceptable oil) or ion exchange resins, or as sparingly soluble derivatives (such as a sparingly soluble salt).

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use with the compounds described above include compositions wherein the active ingredient is contained in a therapeutically effective amount (an amount effective to achieve its intended purpose). Of course, the actual amount effective for a particular application will depend on the viral infection being treated. For example, when administered in methods to treat viral infection, such compositions will contain an amount of active ingredient effective to achieve this result. When administered to patients suffering from viral infections such as amantadine-resistant influenza infections, such compositions will contain an amount of active ingredient effective to prevent or alleviate the existing symptoms of, the patient being treated.

A therapeutically effective dose can also be determined from human data for compounds which are known to exhibit similar pharmacological activities. Adjusting the dose to achieve maximal efficacy in humans based on the methods described above and other methods as are well-known in the art is well within the capabilities of the ordinarily skilled artisan.

In the case of local administration, the systemic circulating concentration of administered compound will not be of particular importance. In such instances, the compound is administered so as to achieve a concentration at the local area effective to achieve the intended result.

Patient doses for oral administration of the compounds described herein for the treatment or prevention of cell proliferative disorders typically range from about 80 mg/day to 16,000 mg/day, more typically from about 800 mg/day to 8000 mg/day, and most typically from about 800 mg/day to 4000 mg/day. Stated in terms of patient body weight, typical dosages range from about 1 to 200 mg/kg/day, more typically from about 10 to 100 mg/kg/day, and most typically from about 10 to 50 mg/kg/day. Stated in terms of patient body surface areas, typical dosages range from about 40 to 8000 mg/m$^2$/day, more typically from about 400 to 4000 mg/m$^2$/day, and most typically from about 400 to 2000 mg/m$^2$/day.

For other modes of administration, dosage amount and interval can be adjusted individually to provide plasma levels of the administered compound effective for the particular clinical indication being treated.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the clinical symptoms demonstrated by the particular patient. Of course, many factors are important in determining a therapeutic regimen suitable for a particular indication or patient.

EXAMPLES

Preparation of 1-(1-adamantyl)cyclohexanamine Also Known as 1-((3r,5r,7r)-adamantan-1-yl)cyclohexan-1-amine (13)

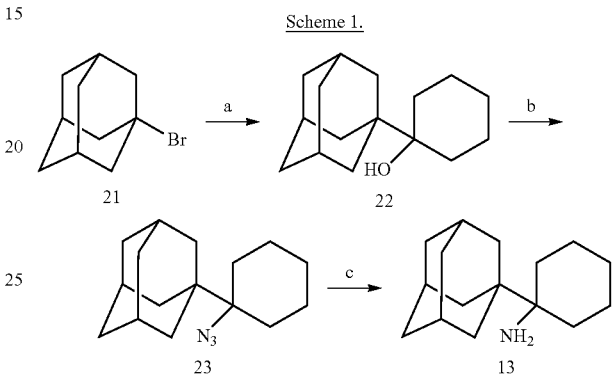

Scheme 1.

Reagents and Conditions: (a) i. Li/THF, sonication ii. cyclohexanone, THF, 0° C. 5 h, and then MeOH—H$_2$O 1:1; (b) NaN$_3$/TFA/CH$_2$Cl$_2$, 0° C. (c) LiAlH$_4$, ether, reflux.

Referring to Scheme 1, tertiary alcohol 22 was obtained from 1-adamantyl lithium (formed by 1-bromoadamantane 21 and lithium wire under sonication) and cyclohexanone in dry THF (yield 70%).

To a stirred mixture of NaN$_3$ (0.170 g, 2.61 mmol) and dry dichloromethane (20 mL) at 0° C., TFA (8.70 mmol) was added. To the stirred mixture a solution of tertiary alcohol 22 (0.204 g, 0.87 mmol) in dry dichloromethane (10 mL) was added and stirring was maintained at 0° C. for 4 hours. The mixture was stirred at ambient temperature for 24 hours and then was treated with NH$_3$ 12% (30 mL) at 0° C. The organic phase was separated and the aqueous phase was extracted twice with an equal volume of dichloromethane. The combined organic phase was washed with water and brine, dried (Na$_2$SO$_4$) and evaporated to afford oily azide 23; yield 0.140 g (65%); IR (Nujol) v (N$_3$) 2101 cm$^{-1}$; $^{13}$C NMR (CDCl$_3$, 50 MHz) δ21.9 (4-cyclohexane-C), 25.6 (3,5-cyclohexane-C), 28.8 (3',5',7'-C), 30.8 (2,6-cyclohexane-C), 35.7 (4',6',10'-C), 37.2 (2',8',9'-C), 42.0 (1'-C), 70.1 (1-cyclohexane-C).

To a stirred suspension of LiAlH$_4$ (65 mg, 1.70 mmol) in dry ether (7 mL) was added, drop-wise at 0° C., a solution of the azide 23 (110 mg, 0.425 mmol) in dry ether (5 mL). The reaction mixture was refluxed for 5 h (TLC monitoring) and then hydrolyzed with water and NaOH (15%) under ice cooling. The inorganic precipitate was filtered off and washed with ether, and the filtrate was extracted with HCl (6%). The aqueous layer was made alkaline with solid Na$_2$CO$_3$ and the mixture was extracted with ether. The combined ether extracts were washed with water and brine and dried (Na$_2$SO$_4$). After evaporation of the solvent the oily amine 13 was obtained; yield: 50 mg (48%); $^1$H NMR (CDCl$_3$, 400 MHz): δ1.35-1.42 (m, 6H, 3,4,5-cyclohexane-H), 1.48-1.55 (m, 3H, 2',8',9'-H), 1.56-1.70 (m, 12H, 2,6- cyclohexane-H, 4',6',10'-H, NH$_2$), 1.98 (br s, 3H, 3',5',7'-H); $^{13}$C NMR (CDCl$_3$, 50 MHz) δ 22.1 (4-cyclohexane-C), 26.4 (3,5-cyclohexane-C), 29.0 (3',5',7'-C), 30.5 (2,6-cyclohexane-C), 35.7 (4',6',10'-C), 37.5 (2',8',9'-C), 38.7 (1'-C), 54.5 (1-cyclohexane-C). Fumarate: mp 264° C. (EtOH-Et$_2$O); Anal. (C$_{20}$H$_{31}$NO$_4$) C, H, N.

Preparation of 1'-methylspiro[pyrrolidine-2,2'-adamantane also called "(1r,3s,5R,7S)-1-methylspiro[adamantane-2,2'-pyrrolidine] and pyrrolidine 1-methylspiro[pyrrolidine-2,2-tricyclo[3.3.1.1$^{3,7}$]decane] (11).

Referring to Scheme 2, a solution of H$_2$NOH HCl (2.29 g, 32.9 mmol) and Na$_2$CO$_3$ (4.18 g, 39.5 mmol) in water (20 mL) was added to a warm solution of 1-methyl-2-adamantanone 24 (1.80 g, 11.0 mmol) in ethanol (60 mL). The mixture was refluxed for 7 hours and allowed to cool at room temperature. Water was added (~70 mL) and the precipitated 1-methyl-2-tricyclo[3.3.1.1$^{3,7}$]decan-2-one oxime 25 was filtered off and washed with water: yield 1.74 g (89%); mp 17° C. (ether); $^1$H-NMR (CDCl$_3$, 400 MHz) δ (ppm) 1.02 (s, 3H, 1-CH$_3$), 1.67-1.69 (m, 4H, 8, 9-H), 1.71-1.82 (m, 4H, 4 eq, 6, 10 eq-H), 1.86 (br d, 2H, J~12 Hz, 4 ax, 10ax-H), 2.0 (br s, 2H, 5, 7-H), 3.63 (br s, 3-H), 9.57 (s, 1H, NOH); $^{13}$C-NMR (CDCl$_3$, 50 MHz) δ (ppm) 24.9 (CH$_3$), 28.3 (7, 5-C), 28.5 (3-C), 35.9 (6-C), 37.85 (4, 10-C), 38.1 (1-C), 46.85 (8,9-C), 168.5 (C=NOH).

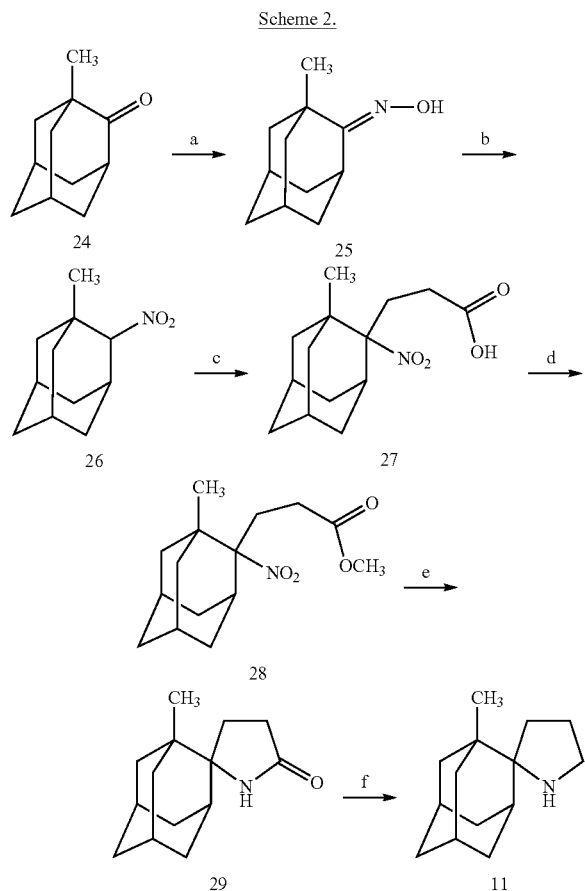

Scheme 2.

Reagents and conditions: (a) H$_2$NOH·HCl, Na$_2$CO$_3$ 90° C., 40 min (93%); (b) i. NBS, NAHCO$_3$, dioxane/water, 10° C., 40 min; ii. HNO$_3$, pentane, 0° C., 15 min; iii. NaBH$_4$, MeOH/H$_2$O; (c) i.CH$_2$=CHCO$_2$Et, Triton-B, t-BuOH, 70° C., 8 h ii. NaOH 1N, EtOH—H$_2$O 3:1, 70° C., 8 h (89%); (d) MeOH/HCl(g), 60° C., 4 h, and then overnight at r.t. (79%); (e) H$_2$/Ni-Raney, EtOH, 50 psi, r.t., 24 h (84%); (f) LiAlH$_4$, THF, reflux, 48 h (60%).

A suspension of the oxime 25 (1.74 g, 9.70 mmol) and NaHCO$_3$ (2.44 g, 29.0 mmol) in a mixture of water (30 mL) and dioxane (80 mL) was added to a vigorously stirred suspension of NBS (5.20 g, 29.1 mmol) in water (30 mL) during a 15 min period at 10° C. Stirring was continued for 40 minutes, and the mixture was extracted with petr. ether. The combined organic extracts were concentrated to a volume of about 30 mL and then treated with nitric acid (30 mL, d=1.42 g mL$^{-1}$) at 0° C. for 15 minutes under vigorous stirring (the blue solution turned into green). Cold water was added (40 mL), the mixture was extracted with petr. ether and the organic layer was washed with water, NaOH 2% and water, and dried (Na$_2$SO$_4$). After solvent evaporation, 1-methyl-2-bromo-2-nitroadamantane was obtained as a crystalline blue solid, which was suspended without purification in a vigorously stirred mixture of methanol (15 mL) and water (5 mL). NaBH$_4$ (1.7 g, 44.8) was promptly added and a very exothermic reaction was observed. The reaction mixture was allowed to cool at room temperature and neutralized with acetic acid. Water was added and the precipitated 1-methyl-2-nitrotricyclo[3.3.1.1$^{3,7}$]decane 26 was filtered off, washed with water, and recrystallized from methanol: yield 1.38 g (73%); $^1$H-NMR (CDCl$_3$, 400 MHz) δ (ppm) 0.91 (s, 3H, 1-CH$_3$), 1.33 (br d, 1H, J~13 Hz, 9 eq-H), 1.50-1.80 (m, 6H, 4, 6, 8 eq, 10 eq-H), 1.85-1.92 (m, 1H, 10ax-H), 1.94 (br t, 1H, J~3 Hz, 5-H), 2.0 (br t, 1H, J~3 Hz, 7-H), 2.12-2.19 (m, 1H, 8ax-H), 2.36-2.41 (m, 3H, 3, 9ax-H); $^{13}$C-NMR (CDCl$_3$, 50 MHz) δ (ppm) 26.5 (1-CH$_3$), 27.2 (7-C), 28.1 (5-C), 30.3 (8-C), 33.4 (3-C), 33.5 (1-C), 36.7 (6-C), 37.3 (10-C), 37.6 (9-C), 45.37 (4-C), 95.4 (2-C).

To a stirred solution of 1-methyl-2-nitroadamantane 26 (1.81 g, 9.28 mmol) and ethyl acrylate (1.86 g, 18.6 mmol) in tert-BuOH (15 mL) was added dropwise a 40% methanolic solution of Triton B (2 mL). An exothermic reaction was observed. The reaction mixture was heated to 70° C. for 8 h, cooled at room temperature and acidified under ice cooling with HCl 3%. The resulting mixture was extracted with ether and the organic phase was washed with water and brine and evaporated under vacuum. The oily residue was treated with a solution of NaOH 1N (1.48 g in 32 mL EtOH/8 mL water) at 80° C. for 6 hours, and the mixture was left overnight at room temperature. After ethanol was evaporated, water was added and the mixture was washed with ether. The aqueous solution was acidified with HCl 18%, and the precipitated acid was filtered off, washed with water and dried to afford 2.3 g (92%) of carboxylic acid 3-(1-methyl-2-nitro-2-tricyclo[3.3.1.1$^{3,7}$]decyl)propanoic acid 27; mp 172° C. (MeOH—H$_2$O); $^1$H-NMR (CDCl$_3$, 400 MHz) δ (ppm) 1.23 (s, 3H, CH$_3$), 1.41 (br d, 1H, J~13 Hz, 9 eq-adamantane H), 1.47 (br d, 1H, J~13 Hz, 8 eq-adamantane H), 1.58-1.70 (m, 4H, 4 eq, 6, 10 eq-adamantane H), 1.72-1.94 (m, 6H, 4ax, 5, 7, 8ax, 9ax, 10ax-adamantane H), 2.26-2.41 (m, 4H, CH$_2$CH$_2$CO$_2$H), 2.53 (s, 1H, 3-adamantine H), 10.7 (CO$_2$H); $^{13}$C-NMR (CDCl$_3$, 50 MHz) δ (ppm) 25.4 (5-CH$_3$), 27.3 (7,5-C), 28.1, 28.2 (CH$_2$CH$_2$CO$_2$H), 33.5 (3-C), 33.6 (10-C), 34.2 (4-C), 37.2 (6-C), 37.7 (1-C), 41.3 (9-C), 44.8 (8-C), 98.9 (2-C), 179.0 (CO$_2$H). Anal. (C$_{14}$H$_{21}$NO$_4$) C, H.

To a stirring methanolic solution of HCl (resulting from adding 7.5 mL of saturated methanolic HCl (43%) in 53 mL dry MeOH) was added portionwise the carboxylic acid 27 (2.2 g, 8.24 mmol) under ice cooling. The resulting solution was heated to 80° C. for 6 hours and left overnight at room temperature. Methanol was evaporated, and ether was added to the oily mixture. The organic solution was washed with water, NaHCO$_3$ 10%, water, brine and dried (Na$_2$SO$_4$). After solvent evaporation the oily methyl 3-(1-methyl-2-nitro-2- tricyclo[3.3.1.1$^{3,7}$]decyl)propanoate 28 was obtained (1.83 g, 79%); IR (Nujol) v (C=O) 1741, v (NO$_2$) 1535 cm$^{-1}$.

A solution of the nitroester 28 (1.83 g, 6.51 mmol) in ethanol (35 mL) was hydrogenated for 24 hours under pressure (50 psi) at 50° C. over Raney-Nickel catalyst. Catalyst was filtered off, the filtrate was evaporated under vacuum and the residue was flash chromatographed on silical gel (35-70 μm) with methanol/ether 1:2 as an eluent to afford the solid lactam 1-methylspiro[pyrrolidine-2,2-tricyclo[3.3.1.1$^{3,7}$]decan]-5-one 29 (990 mg, 69%); mp 169° C. (ether-n-pentane); $^1$H-NMR (CDCl$_3$, 400 MHz) δ (ppm) 0.74 (s, 3H, 1-CH$_3$), 1.33 (dt, 1H, J~2, 13 Hz, 9 eq-H), 1.39 (dt, 1H, J~2, 13 Hz 8 eq-H), 1.55-1.61 (m, 2H, 8ax, 9ax-H), 1.64-1.83 (m, 8H, 3, 3,4,6,10-H), 1.88 (br p, 1H, J~2 Hz, 7-H), 1.91 (br p, 1H, J~2 Hz, 5-H), 2.18-2.26 (m, 2H, 3-H), 2.31-2.36 (m, 2H, 4-H); $^{13}$C-NMR (CDCl$_3$, 50 MHz) δ (ppm) 23.7 (1-CH$_3$), 28.0 (7, 5-C), 28.6 (3-C), 31.2 (4-C), 33.9, 34.0 (4, 10-C), 36.4 (1-C), 37.2 (6-C), 40.4 (3-C), 41.0, 41.5 (8, 9-C), 66.6 (2-C), 177.7 (5-C). Anal. (C$_{14}$H$_{21}$NO) C, H.

To a stirred suspension of LiAlH$_4$ (1.0 g, 17.6 mmol) in dry THF (50 mL) was added dropwise a solution of the lactam 29 (770 mg, 3.52 mmol) in dry THF (20 mL). The reaction mixture was refluxed for 48 h and then hydrolyzed with water and NaOH (15%) and water under ice cooling. The inorganic precipitate was filtered off and washed with THF, and the filtrate was concentrated in vacuo. The residue was dissolved in ether and extracted with HCl (6%). The aqueous layer was made alkaline with solid Na$_2$CO$_3$ and the oily product formed was extracted with ether. The combined ether extracts were washed with water and brine and dried (Na$_2$SO$_4$). After evaporation of the solvent, the residue was flash chromatographed on silical gel (35-70 μm) with methyl acetate-methanol 4/1 as an eluent to give the oily pyrrolidine 1-methylspiro [pyrrolidine-2,2-tricyclo[3.3.1.1$^{3,7}$]decane] 11: (430 mg, 60%); $^1$H-NMR (CD$_2$Cl$_2$, 400 MHz) δ (ppm) 0.74 (s, 3H, 1-CH$_3$), 1.22 (br d, 1H, J~13 Hz, 9 eq-H), 1.36 (dt, 1H, J=2.4, 13 Hz, 8 eq-H), 1.51-1.59 (m, 4H, 3, 4 eq, 3ax-H, NH), 1.60-1.75 (m, 6H, 6, 8ax, 10 eq, 4-H), 1.76-1.82 (m, 3H, 5, 7, 10ax-H), 1.85-1.92 (m, 1H, 3 eq-H), 1.92 (1H, J~13 Hz, 9ax-H), 2.02 (br d, 1H, J~12 Hz, 4ax-H), 2.95 (m, 2H, 5-H), 5.28 (s, 1H, NH); (CDCl$_3$, 400 MHz) δ (ppm) 0.74 (s, 3H, 1-CH$_3$), 1.23 (br d, 1H, J~13 Hz, 9 eq-H), 1.36 (br d, 1H, J~13 Hz, 8 eq-H), 1.50-1.60 (m, 4H, 3, 4 eq, 3ax-H, NH), 1.61-1.80 (m, 5H, 6, 8ax, 10 eq, 4-H), 1.82-1.97 (m, 5, 7, 9ax, 10ax, 3 eq-H), 2.0 (br d, 1H, J~12 Hz, 4ax-H), 2.97 (t, 2H, J~6 Hz, 5-H); $^{13}$C-NMR (CD$_2$Cl$_2$, 50 MHz) δ (ppm) 24.1 (1-CH$_3$), 26.6 (4-C), 28.3 (7-C), 28.4 (5-C), 32.6 (3-C), 34.0 (10-C), 35.3 (4-C), 35.9 (1-C), 37.4 (6-C), 38.7 (3-C), 41.6 (9-C), 42.9 (8-C), 47.3 (5-C), 85.2 (2-C). Fumarate: mp 163° C. dec. (EtOH-Et$_2$O); Anal. (C$_{18}$H$_{27}$NO$_4$) C, H.

Preparation of N-aminoethylspiro[pyrrolidine-2,2'-adamantane also called 2-((1r,3r,5r,7r)-spiro[adamantane-2,2'-pyrrolidin]-1'-yl)ethan-1-amine and 1-(2-aminoethyl)spiro [pyrrolidine-2,2'-tricyclo[3.3.1.1$^{3,7}$]decane] (12).

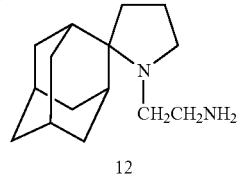

12

Reagents and conditions: a) BrCH$_2$CONH$_2$, Et$_3$N, THF, r.t., 24 h (34%);
b) LiAlH4, THF, reflux, 27 h (76%).

Referring to Scheme 3, to a stirred solution of the spiropyrrolidine 8 (800 mg, 4.20 mmol) and triethylamine (450 mg 4.46 mmol) in dry THF (15 mL) was added dropwise a solution of bromoacetamide (610 mg, 4.20 mmol) in dry THF (10 mL) under ice-cooling. The reaction mixture was stirred at room temperature for 24 hours, filtered off and the filtrate was evaporated under vacuum. The residue was dissolved in dichloromethane and the organic solution was washed with water, dried (Na$_2$SO$_4$) and evaporated under vacuum. After treatment of the oily residue with pentane, the solid spiro[pyrrolidine-2,2'-tricyclo[3.3.1.1$^{37}$]decane]-1-acetamide 30 was obtained: yield 350 mg (34%); IR (Nujol) v (NH$_2$) 3419 cm$^{-1}$, v (C=O) 1686 cm$^{-1}$; $^1$H-NMR (CDCl$_3$, 400 MHz) δ (ppm) 1.46-1.56 (m, 2H, 4'eq, 9'eq-H), 1.62-1.88 (m, 14H, 1', 3', 5', 6', 7', 8', 10'-adamantane H, 3, 4-H), 1.98-2.12 (m, 2H, 4'ax, 9'ax-H), 2.71-2.82 (t, J~13 Hz, 2H, 5-H), 2.96 (s, 2H, CH$_2$CO), 5.85 (br s, 1H, NH), 7.35 (br s, 1H, NH).

To a stirred suspension of LiAlH$_4$ (320 mg, 8.47 mmol) in dry THF (25 mL) was added dropwise at 0° C. a solution of the acetamide 30 (350 mg, 1.41 mmol) in dry THF (10 mL). The reaction mixture was refluxed for 27 h (TLC monitoring) and then hydrolyzed with water and NaOH (15%) and water under ice cooling. The inorganic precipitate was filtered off and washed with THF, and the filtrate was evaporated under vacuum. The residue was flash chromatographed on silical gel (35-70 μm) with methanol. The organic solution was evaporated under vacuum and ether was added. The resulting mixture was filtered off and the filtrate was evaporated in vacuo to afford 250 mg of the oily diamine 12: yield 76%; $^1$H NMR (CDCl$_3$, 400 MHz): δ 1.44 (br d, J~12 Hz, 2H, 4'eq, 9'eq-H), 1.50-1.88 (m, 16H, 1', 3', 5', 6', 7', 8', 10'-adamantane H, 3, 4-H, NH$_2$), 2.24 (br d, J~12 Hz, 2H, 4'ax, 9'ax-H), 2.28-2.34 (t, J~6 Hz, 2H, CH$_2$N), 2.70-2.79 (m, 4H, 5-H, CH$_2$NH$_2$); $^{13}$C NMR (CDCl$_3$, 50 MHz) δ21.3 (4-C), 27.6, 27.7 (7', 5'-C), 30.9 (3-C), 33.4 (4, 9-C), 33.5 (1', 3'-C), 35.2 (8, 10'-C), 38.3 (6-C), 41.8 (CH$_2$N), 47.6 (5-C), 48.5 (CH$_2$NH$_2$), 70.4 (2-C). Bifumarate: mp 144-145° C. dec. (EtOH-Et$_2$O); Anal. (C$_{23}$H$_{34}$N$_2$O$_8$) C, H.

Preparation of 2-n-Butyl-tricyclo[3.3.1.1$^{3,7}$]decan-2-amine also known as (1r,3r,5r,7r)-2-butyladamantan-2-amine (17).

Scheme 3.

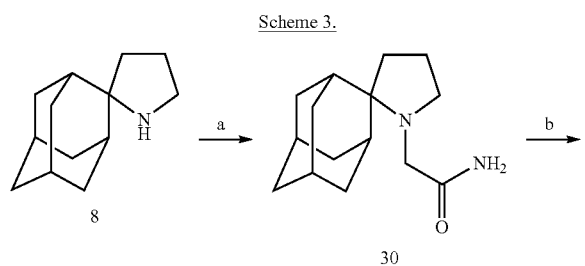

Scheme 4.

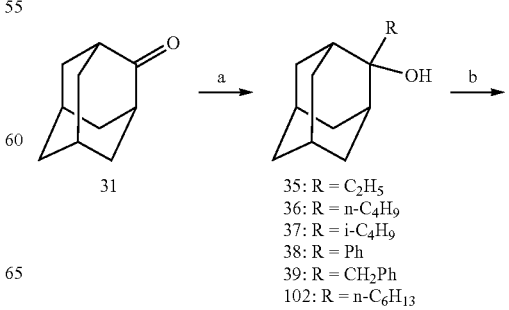

35: R = C$_2$H$_5$
36: R = n-C$_4$H$_9$
37: R = i-C$_4$H$_9$
38: R = Ph
39: R = CH$_2$Ph
102: R = n-C$_6$H$_{13}$

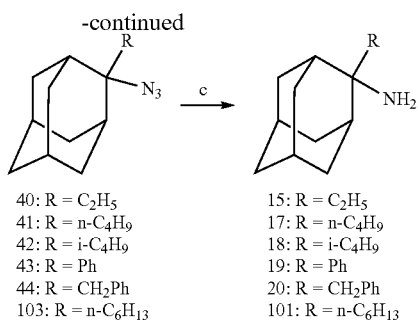

40: R = C₂H₅
41: R = n-C₄H₉
42: R = i-C₄H₉
43: R = Ph
44: R = CH₂Ph
103: R = n-C₆H₁₃

15: R = C₂H₅
17: R = n-C₄H₉
18: R = i-C₄H₉
19: R = Ph
20: R = CH₂Ph
101: R = n-C₆H₁₃

Referring to Scheme 4, tertiary alcohol 36 was obtained after treating a solution of adamantanone 31 in dry THF (30% solution w/v) with n-butyllithium (1.6 M in hexanes) at 0° C. with 3 molar excess and stirring the mixture overnight; yield 96%; ¹H NMR (CDCl₃, 400 MHz): δ0.91 (t, J~7 Hz, 3H, CH₃), 1.25-1.38 (m, 4H, CH₃CH₂CH₂CH₂), 1.54 (d, J~12 Hz, 2H, 4'eq, 9'eq-H), 1.58-1.72 (m, 8H, 1',3',5',7',8'eq, 10'eq-H, CH₃CH₂CH₂CH₂), 1.78-1.90 (m, 4H, 8'ax, 10'ax-H, 5',7'-H), 2.16 (d, J~12 Hz, 1H, 4'ax, 9'ax-H); ¹³C NMR (CDCl₃, 50 MHz) δ14.3 (CH₃), 23.5 (CH₂CH₂CH₂CH₃), 24.4 (CH₂CH₂CH₂CH₃), 27.4, 27.6 (5', 7'-C), 33.1 (8',10'-C), 34.7 (4',9'-C), 37.1 (1',3'-C), 38.2 (CH₂CH₂CH₂CH₃), 38.5 (6'-C), 75.2 (2'-C).

To a stirred mixture of NaN₃ (4.32 mmol) and dry dichloromethane (20 mL) at 0° C., TFA (14.4 mmol) was added. To the stirred mixture, a solution of tertiary alcohol 36 (1.44 mmol) in dry dichloromethane (10 mL) was added and stirring was maintained at 0° C. for 4 hours. The mixture was stirred at ambient temperature for 24 hours and then was treated with NH₃ 12% (30 mL) at 0° C. The organic phase was separated and the aqueous phase was extracted twice with an equal volume of dichloromethane. The combined organic phase was washed with water and brine, dried (Na₂SO₄) and evaporated to afford oily azide 41; yield 96%; ¹H NMR (CDCl₃, 400 MHz): δ 0.96 (t, J~7 Hz, 3H, CH₃), 1.32-1.42 (m, 4H, CH₃CH₂CH₂CH₂), 1.62 (d, J~12 Hz, 2H, 4'eq, 9'eq-H), 1.70-1.93 (m, 12H, adamantane-H, CH₃CH₂CH₂CH₂), 2.14 (d, J~12 Hz, 1H, 4'ax, 9'ax-H); ¹³C NMR (CDCl₃, 50 MHz) δ14.2 (CH₃), 23.3 (CH₂CH₂CH₂CH₃), 24.9 (CH₂CH₂CH₂CH₃), 27.2, 27.4 (5',7'-C), 33.7 (8',10'-C), 33.8 (4',9'-C), 34.4 (1',3'-C), 35.2 (CH₂CH₂CH₂CH₃), 38.5 (6'-C), 69.7 (2'-C).

To a stirred suspension of LiAlH₄ (163 mg, 4.29 mmol) in dry ether (15 mL) was added dropwise at 0° C. a solution of the azide 41 (250 mg, 1.07 mmol) in dry ether (10 mL). The reaction mixture was refluxed for 5 hours (TLC monitoring), and then hydrolyzed with water and NaOH (15%) and water under ice cooling. The inorganic precipitate was filtered off and washed with ether, and the filtrate was extracted with HCl (6%). The aqueous layer was made alkaline with solid Na₂CO₃ and the mixture was extracted with ether. The combined ether extracts were washed with water and brine and dried (Na₂SO₄). After evaporation of the solvent the oily amine 17 was obtained; yield 50 mg (23%); ¹H NMR (CDCl₃, 400 MHz): δ 0.88 (t, J~7 Hz, 3H, CH₃), 1.18-1.32 (m, 4H, CH₃CH₂CH₂CH₂), 1.45-165 (m, 10H, adamantane-H, CH₃CH₂CH₂CH₂), 1.77 (br s, 2H, 5',7'-H), 1.93 (d, J~12 Hz, 2H, 8'ax, 10'ax-H), 2.03 (d, J~12 Hz, 2H, 4'ax, 9'ax-H), 2.13 (-br s, 2H, NH₂); ¹³C NMR (CDCl₃, 50 MHz) δ 14.3 (CH₃), 23.7 (CH₂CH₂CH₂CH₃), 24.6 (CH₂CH₂CH₂CH₃), 27.5, 27.8 (5',7'-C), 33.2 (8',10'-C), 34.1 (4',9'-C), 37.5 (1',3'-C), 38.6 (6'-C), 39.1 (CH₂CH₂CH₂CH₃), 54.5 (2'-C). Hydrochloride: mp>250° C. (EtOH-Et₂O); Anal. (C₁₄H₂₆NCl) C, H.

Preparation of 2-i-Butyl-tricyclo[3.3.1.1³,⁷]decan-2-amine also known as (1r,3r,5r,7r)-2-isobutyladamantan-2-amine (18).

Referring again to Scheme 4, tertiary alcohol 37 was obtained after treating a solution of 2-adamantanone 31 in dry THF with i-butyllithium (1.6 M in hexanes) at 0° C. in a 1:3 ratio as before; yield 85%; ¹H NMR (CDCl₃, 400 MHz): δ 0.96 (d, J~7 Hz, 6H, 2×CH₃), 1.52 (d, J~12 Hz, 2H, 4'eq, 9'eq-H), 1.57 (d, J~6 Hz, 2H, CH₂CHMe₂), 1.66 (1',3',6'-H), 1.68-1.74 (m, 2H, 8'eq,10'eq-H), 1.78 (br s, 2H, 5',7'-H), 1.76-1.87 (m, 1H, CH₂CHMe₂), 1.82 (m, 2H, 8'ax, 10'ax-H); ¹³C NMR (CDCl₃, 50 MHz) δ23.2 (2×CH₃), 25.3 (CH₂CHMe₂), 27.5 (5',7'-C), 33.1 (8',10'-C), 35.1 (4',9'-C), 37.6 (1',3'-C), 38.5 (6'-C), 46.5 (CH₂CHMe₂), 75.9 (2'-C). The corresponding azide 42 was prepared according to the same procedure followed for azide 41 using CH₂Cl₂/NaN₃/TFA; yield 95%; ¹³C NMR (CDCl₃, 50 MHz) 23.4 (2×CH₃), 24.5 (CH₂CHMe₂), 27.3 (5',7'-C), 33.6 (8',10'-C), 33.9 (4', 9'-C), 34.7 (1',3'-C), 38.5 (6'-C), 43.0 (CH₂CHMe₂), 69.7 (2'-C).

The corresponding oily amine 18 was prepared through LiAlH₄ reduction in refluxing ether for 5 hours according to the same procedure followed for amine 17; yield 65%; ¹H NMR (CDCl₃, 400 MHz): δ0.94 (d, J~7 Hz, 6H, 2×CH₃), 1.49 (d, J~6 Hz, 2H, CH₂CHMe₂), 1.52-1.65 (m, 2H, 1',3',6',4'eq,9'eq-H), 1.73-1.83 (m, 1H, CH₂CHMe₂), 1.75 (br s, 2H, 5',7'-H), 1.95 (d, J~12 Hz, 2H, 8'ax, 10'ax-H), 2.05 (d, J~12 Hz, 2H, 4'ax, 9'ax-H); ¹³C NMR (CDCl₃, 50 MHz) δ23.4 (2×CH₃), 25.7 (CH₂CHMe₂), 27.6 (5',7'-C), 33.1 (8',10'-C), 34.3 (4',9'-C), 38.0 (1',3'-C), 39.1 (6'-C), 47.4 (CH₂CHMe₂), 55.4 (2'-C). Hydrochloride: mp>250° C. (EtOH-Et₂O); Anal. (C₁₄H₂₆NCl) C, H.

Preparation of 2-Phenyl-tricyclo[3.3.1.1³,⁷]decan-2-amine also known as (1r,3r,5r,7r)-2-phenyladamantan-2-amine (19).

Referring again to Scheme 4, tertiary alcohol 38 was obtained after treating a solution of adamantanone 31 in dry THF (30% solution w/v) with 2-molar excess PhMgBr (obtained from bromobenzene, 1.5 molar excess of Mg, in 20 mL of dry ether/g bromobenzene) and stirring the mixture overnight; yield 95%; ¹H NMR (CDCl₃, 400 MHz): δ1.67-1.77 (m, 8H, adamantane-H), 1.89 (br s, 2H, 5',7'-H), 2.14 (s, 1H, OH), 2.40 (d, J~12 Hz, 1H, 4'ax, 9'ax-H), 2.56 (br s, 2H, 1',3'-H), 7.20-7.60 (m, 5H, phenyl-H); ¹³C NMR (CDCl₃, 50 MHz) δ 27.0, 27.5 (5',7'-C), 33.1 (8',10'-C), 34.9 (4',9'-C), 35.7 (1',3'-C), 37.8 (6'-C), 75.8 (2'-C), 125.5, 127.1, 127.2, 128.8, 143.0 (Ph).

The corresponding azide 43 was prepared according to the same procedure followed for azide 41 using CH₂Cl₂/NaN₃/TFA; yield 95%; ¹³C NMR (CDCl₃, 50 MHz) δ 26.8, 27.4 (5',7'-C), 33.1 (8',10'-C), 33.4 (4',9'-C), 34.1 (1',3'-C), 37.7 (6'-C), 70.3 (2'-C), 125.6, 127.3, 127.8, 128.9, 140.3 (Ph).

The corresponding oily amine 19 was prepared through LiAlH₄ reduction in refluxing ether for 5 h according to the same procedure followed for amine 17; yield 55%; ¹H NMR (CDCl₃, 400 MHz): δ1.53 (br s, 2H, 6'-H), 1.61-1.80 (m, 6H, adamantane-H), 1.90 (br s, 2H, 5',7'-H), 2.33 (d, J~12 Hz, 1H, 4'ax, 9'ax-H), 2.45 (br s, 2H, 1',3'-H), 7.18-7.25 (m, 5H, phenyl-H); ¹³C NMR (CDCl₃, 50 MHz) δ 27.2, 27.6 (5',7'-C), 32.9 (8',10'-C), 34.6 (4',9'-C), 35.8 (1',3'-C), 38.2 (6'-C), 57.8 (2'-C), 125.2, 126.2, 128.8, 148.7 (Ph). Hydrochloride: mp>250° C. (EtOH-Et₂O); Anal. (C₁₆H₂₂NCl) C, H.

Preparation of 2-Benzyl-tricyclo[3.3.1.1$^{3,7}$]decan-2-amine also known as (1r,3r,5r,7r)-2-benzyladamantan-2-amine (20).

Referring again to Scheme 4, tertiary alcohol 39 was obtained after treating a solution of adamantanone 31 in dry THF (30% solution w/v) with 2-molar excess PhCH$_2$MgCl (obtained from PhCH$_2$Cl, 1.5 molar excess of Mg, in 20 mL of dry ether/g bromobenzene) and stirring the mixture overnight; yield 95%; $^1$H NMR (CDCl$_3$, 400 MHz): δ1.51 (d, J~12 Hz, 2H, 4'eq, 9'eq-H), 1.65 (br s, 1H, 6'-H), 1.69 (br s, 1H, 5',7'-H), 1.77 (d, J~12 Hz, 2H, 8'eq, 10'eq-H), 1.78 (br s, 1H, 3'-H), 1.90 (br s, 1H, 1'-H), 2.07 (d, J~12 Hz, 1H, 8'ax, 10'ax-H), 2.12 (d, J~12 Hz, 1H, 4'ax, 9'ax-H), 2.97 (s, 2H, CH$_2$Ph), 7.10-7.32 (m, 5H, phenyl-H); $^{13}$C NMR (CDCl$_3$, 50 MHz) δ 27.4, 27.5 (5',7'-C), 33.1 (8',10'-C), 34.7 (4',9'-C), 36.9 (1',3'-C), 38.5 (6'-C), 43.9 (CH$_2$Ph), 74.7 (2'-C), 126.5, 128.3, 130.7, 137.4 (Ph).

The corresponding azide 44 was prepared according to the same procedure followed for azide 41 using CH$_2$Cl$_2$/NaN$_3$/TFA; yield 50%; $^{13}$C NMR (CDCl$_3$, 50 MHz) δ 27.1, 27.4 (5',7'-C), 33.7 (8',10'-C), 33.8 (4',9'-C), 34.1 (1',3'-C), 38.4 (6'-C), 41.4 (CH$_2$Ph), 69.8 (2'-C), 126.7, 128.2, 130.3, 13663 (Ph).

The corresponding oily amine 20 was prepared through LiAlH$_4$ reduction in refluxing ether for 5 h according to the same procedure followed for amine 17; yield 45%; $^1$H NMR (CDCl$_3$, 400 MHz): δ1.61 (d, J~12 Hz, 2H, 4'eq, 9'eq-H), 1.61 (br s, 1H, 6'-H), 1.73 (br s, 1H, 5',7'-H), 1.78 (d, J~12 Hz, 2H, 8'eq, 10'eq-H), 1.87 (br s, 1H, 3'-H), 1.97 (br s, 1H, 1'-H), 2.09 (d, J~12 Hz, 1H, 8'ax, 10'ax-H), 2.29 (d, J~12 Hz, 1H, 4'ax, 9'ax-H), 2.97 (s, 2H, CH$_2$Ph), 7.10-7.32 (m, 5H, phenyl-H); $^{13}$C NMR (CDCl$_3$, 50 MHz) δ 27.6, 27.8 (5',7'-C), 33.2 (8',10'-C), 34.3 (4',9'-C), 37.3 (1',3'-C), 39.2 (6'-C), 44.2 (CH$_2$Ph), 55.1 (2'-C), 126.3, 128.1, 130.7, 138.4 (Ph). Hydrochloride: mp>250° C. (EtOH-Et$_2$O); Anal. (C$_{17}$H$_{24}$NCl) C, H.

Preparation of 2-n-hexyl-tricyclo[3.3.1.1$^{3,7}$]decan-2-amine (101)

Referring again to Scheme 4, the preparation of this amine was based on reaction of n-hexyl lithium with 2-adamantanone 31 following the same procedure described above for compounds 35 and 40. Yield 97%; $^1$H NMR (CDCl$_3$, 400 MHz): δ 0.87 (t, J~7 Hz, 3H, CH$_3$), 1.24-1.30 (m, 8H, CH$_2$(CH$_2$)$_4$CH$_3$), 1.51-156 (m, 4H, 4'eq, 9'eq-H, CH$_2$(CH$_2$)$_4$CH$_3$), 1.57-1.67 (m, 6H, 1',3',6',8'eq, 10'eq-H), 1.79 (br s, 2H, 5',7'-H), 1.93 (d, J~12 Hz, 2H, 8'ax, 10'ax-H), 2.04 (d, J~12 Hz, 2H, 4'ax, 9'ax-H); $^{13}$C NMR (CDCl$_3$, 50 MHz) δ 14.2 (CH$_3$), 22.3 ((CH$_2$)$_4$CH$_2$CH$_3$), 22.8 ((CH$_2$)$_3$CH$_2$CH$_2$CH$_3$), 27.4-27.8 (5',7'-C), 30.3 (CH$_2$CH$_2$CH$_2$(CH$_2$)$_2$CH$_3$), 32.0 (CH$_2$CH$_2$(CH$_2$)$_3$CH$_3$), 33.1 (4',9'-C), 34.1 (8',10'-C), 37.4 (1',3'-C), 38.8 (CH$_2$(CH$_2$)$_4$CH$_3$), 39.1 (6'-C), 54.6 (2'-C). Fumarate: mp 225° C. (EtOH-Et$_2$O); Anal. (C$_{18}$H$_{29}$NO$_4$) C, H, N.

Compounds of Formula VI are shown in Scheme 8. Preparation of 2-(adamantan-1-yl)propan-2-amine (259).

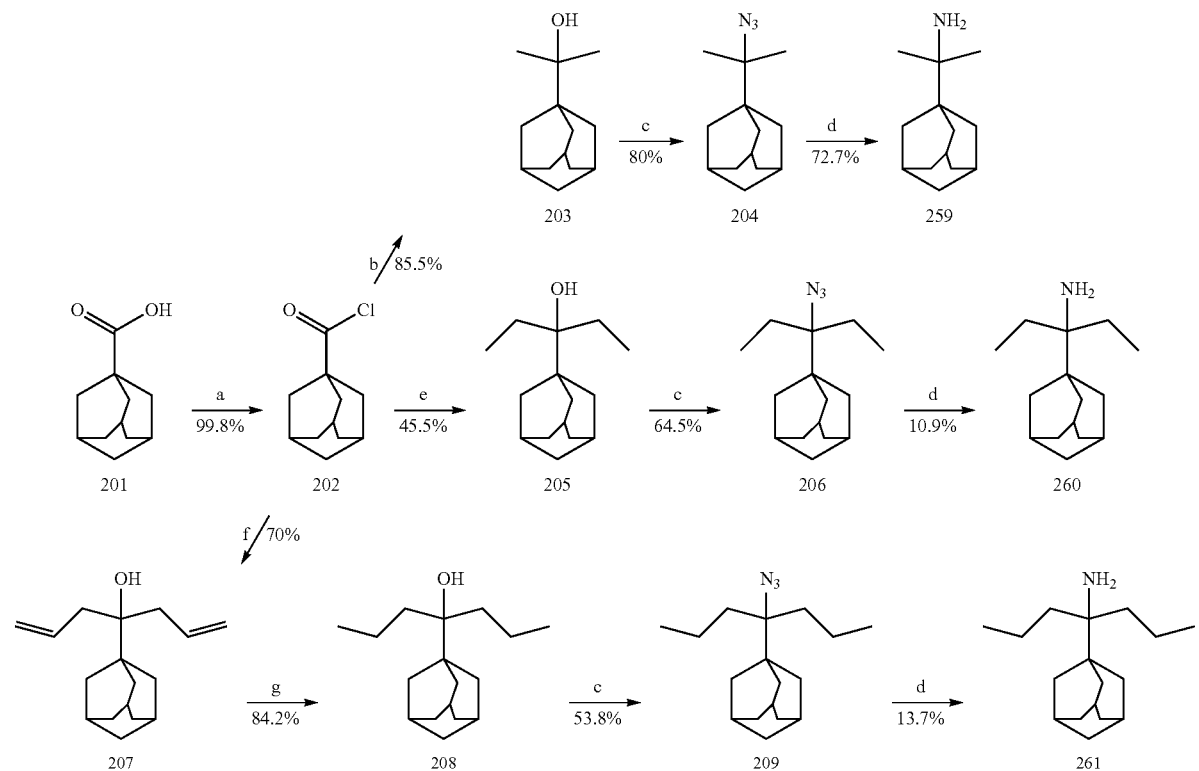

Scheme 8.

Reagents and Conditions: (a) SOCl2/reflux/2 h; (b) i. MeMgI/dry ether ii. gentle reflux/Ar atm/4 h; (c) NaN3/TFA/CH2Cl2/0° C./4 h; (d) LiAlH4/dry ether/reflux/5h; (e) EtLi/benzene/cyclohexane/Ar atm/26 h; (f) i. AllylMgBr/dry ether ii. gentle reflux/Ar atm/4 hl; (g) H2PtO2/EtOH/20 h.

Referring to Scheme 8, the thionyl chloride used in the reaction of step a was purified using a distillation column in presence of quinoline to retain any hydrochloric acid as hydrochloric salt. Thionyl chloride (6 mL, 83.3 mmol) was added in 1-adamantanecarboxylic acid 201 (3 g, 16.7 mmol) and the mixture was heated at reflux while stirring for 2 hours, then evaporated under vacuum. The residue was washed with 30 mL of benzene (3×10 mL) and then dried to yield a yellow colored solid residue of 1-adamantanecarbonyl chloride 202. Yield 3.32 g (99.8%); IR (Nujol) v (C=O) 1787 cm$^{-1}$ (s); $^1$H-NMR (400 MHz, CDCl$_3$) δ 1.72 (q, 6H), 1.97 (d, 6H), 2.08 (br s, 3H); $^{13}$C-NMR (200 MHz, CDCl$_3$) δ: 28.3 ($C_{3',5',7'}^{Ad}$), 36.22 ($C_{4',6',10'}^{Ad}$), 39.16 ($C_{2',8',9'}^{Ad}$), 51.29 ($C_{1'}^{Ad}$), 180.09 (C=O).

The Grignard reagent was prepared from magnesium turnings (1.99 g, 83.1 mmol) and methyl iodide (10.7 g, 75.6 mmol) in 40 mL of dry diethyl ether. A solution of 1-adamantanecarbonyl chloride 202 (2.5 g, 12.6 mmol) in 60 mL of dry diethyl ether was added dropwise under Ar atmosphere and stirring. The reaction mixture was heated at gentle reflux for 4 hours under stirring and Ar atmosphere. The mixture was treated with an equal volume of saturated solution of ammonium chloride under ice-cooling. The organic layer was separated and the aqueous phase was extracted with diethyl ether 2 times. The combined organic phases were washed with water and brine, dried (Na$_2$SO$_4$) and evaporated under vacuum to yield a white colored solid residue of 2-(1-adamantyl)-propan-2-ol 203. Yield 2.09 g (85.5%); IR (Nujol): v (OH) 3400 (br.s, O—H) cm$^{-1}$; $^1$H-NMR (400 MHz, CDCl$_3$) δ: 1.12 (s, 6H), 1.63 (d, 9H), 1.67 (d, 3H), 1.99 (br s, 3H); $^{13}$C-NMR (200 MHz, CDCl$_3$) δ: 24.34 (CH$_3$), 28.74 ($C_{3',5',7'}^{Ad}$) 36.35 ($C_{4',6',10'}^{Ad}$), 37.22 ($C_{2',8',9'}^{Ad}$), 38.84 ($C_{1'}^{Ad}$), 74.88 (C—OH).

Trifluoroacetic acid (2.94 g, 25.8 mmol) was added dropwise to a mixture of sodium azide (503 mg, 7.74 mmol) in 15 mL of dry dichloromethane at 0° C. under stirring. Stirring was continued for 10 minutes under ice-cooling, and then a solution of 2-(1-adamantyl)-propan-2-ol 203 (500 mg, 2.58 mmol) in 15 mL of dry dichloromethane was added dropwise under ice-cooling. The mixture was stirred vigorously for 4 hours under ice-cooling and additionally 24 hours at room temperature. The mixture was made alkaline with 30 mL of ammonia 12% w/v solution under ice-cooling. The organic layer was separated and washed with 30 mL of water twice. The aqueous phase was extracted 2 times with 30 mL of dichloromethane. The combined organic extracts were dried (Na$_2$SO$_4$) and evaporated under vacuum to yield a yellow colored oil residue of 2-(1-adamantyl)-propan-2-azide 204. Yield: 450 g (80%); IR (Nujol): v (N3) 2098 cm$^{-1}$ (s); $^1$H-NMR (400 MHz, CDCl$_3$) δ: 1.23 (s, 6H), 1.61 (br s, 9H), 1.67-1.70 (d, 3H), 2 (br s, 3H); $^{13}$C-NMR (200 MHz, CDCl$_3$) δ: 20.79 (CH$_3$), 28.66 ($C_{3',5',7'}^{Ad}$), 36.56 ($C_{4',6',10'}^{Ad}$) 37.07 ($C_{2',8',9'}^{Ad}$), 39.10 ($C_{1'}^{Ad}$), 67.57 (C—N).

A solution of 2-(1-adamantyl)-propan-2-azide 204 (250 mg, 1.14 mmol) in 10 mL of dry diethyl ether was added dropwise to a solution of lithium aluminum hydride (173 mg, 4.56 mmol) in 10 mL of dry diethyl ether under ice-cooling. The mixture was heated at reflux for 5 hours under stirring. Then the mixture was hydrolyzed with a dropwise addition of 2 mL water, 2 mL of sodium hydroxide 10% w/v solution and 6 mL water under stirring and ice-cooling. The mixture was filtered under vacuum and the residue was washed 2 times with diethyl ether. Another 30 mL of diethyl ether was added to the ethereal filtrate and the solution was extracted with 60 mL (2×30 mL) of hydrochloric acid 6% w/v. The aqueous phase was separated and made alkaline through-addition of an excess solid sodium carbonate under ice-cooling. The aqueous phase was extracted twice with 30 mL of dichloromethane. The combined organic extracts were dried (Na$_2$SO$_4$) and evaporated under vacuum, to yield a light yellow colored solid residue of 2-(1-adamantyl)-propan-2-amine 259. Yield: 160 mg (72.7%); IR (Film): v (NH$_2$) 3373 cm$^{-1}$ (s); $^1$H-NMR (400 MHz, CDCl$_3$) δ: 0.99 (s, 6H), 1.60 (br.s, 9H), 1.66 (d, 3H), 1.99 (br.s, 3H); $^{13}$C-NMR (200 MHz, CDCl$_3$) δ: 25.30 (CH$_3$), 28.87 ($C_{3',5',7'}^{Ad}$), 36.23 ($C_{4',6'10'}^{Ad}$), 37.26 ($C_{2',8',9'}^{Ad}$), 38.12 ($C_{1'}^{Ad}$), 53.68 (C—N).

Preparation of 3-(adamantan-1-yl)pentan-3-amine (260)

Referring to Scheme 8, a solution of 1-adamantanecarbonyl chloride 202 (700 mg, 3.53 mmol) in 25 mL of dry diethyl ether was added dropwise under Ar atmosphere and stirring, to a solution of 5 mL ethyl lithium (0.5 M, 12.5 mmol) in benzene/cyclohexane. The mixture was stirred for 26 hours under Ar atmosphere at room temperature. The reaction mixture was hydrolyzed with an equal volume of saturated ammonium chloride solution under ice-cooling. The organic layer was separated and the aqueous phase was extracted with diethyl ether twice. The combined organic phase was washed twice with a solution of sodium hydroxide 3% w/v, water and brine, and dried over anhydrous sodium sulfate. After evaporation of the solvent under vacuum, a light yellow colored solid residue of the alcohol 205 was obtained. Yield 357 mg (45.5%); IR (Nujol): v (OH) 3502 cm$^{-1}$ (br s); $^1$H-NMR (400 MHz, CDCl$_3$) δ: 0.93 (t, 6H), 1.56 (q, 4H), 1.68 (m, 12H), 2.05 (br.s, 3H); $^{13}$C-NMR (200 MHz, CDCl$_3$) δ: 9.47 (CH$_3$), 25.93 (CH$_2$), 28.90 ($C_{3',5',7'}^{Ad}$), 36.71 ($C_{4',6',10'}^{Ad}$), 37.40 ($C_{2',8',9'}^{Ad}$), 38.51 ($C_{1'}^{Ad}$), 40.48 (C—OH).

Trifluoroacetic acid (1.8 g, 15.8 mmol) was added dropwise to a mixture of sodium azide (308 mg, 4.74 mmol) in 20 mL of anhydrous dichloromethane at 0° C., under stirring. Stirring was continued for 10 min under ice-cooling, and a solution of 3-(1-adamantyl)-pentan-3-ol 205 (350 mg, 1.58 mmol) in 5 mL of dry dichloromethane was added dropwise under ice-cooling. The mixture was stirred vigorously for 4 hours under ice-cooling and an additional 24 hours at room temperature. The mixture was made alkaline with 30 mL of ammonia 12% w/v solution under ice-cooling. The organic layer was separated and washed with 30 mL of water twice. The aqueous phase was extracted twice with 30 mL of dichloromethane. The combined organic extracts were dried (Na$_2$SO$_4$) and evaporated under vacuum to yield 160 mg of a yellow colored oily product consisting of 103 mg (64.5%) of the desired 3-(1-adamantyl)-pentan-3-azide 206 and 57 mg (35.5%) of 3-(1-adamantyl)-pent-2-ene-as an elimination byproduct. IR (Flim) v (=C—H): 3056 cm$^{-1}$ (m), v (N$_3$) 2095 cm$^{-1}$ (s), v (C=C) 1601 cm$^{-1}$ (w). The crude oily mixture was used without further purification for the LiAlH$_4$ reduction step.

A solution of the crude azide 206 (160 mg) in 4 mL of dry diethyl ether was added dropwise to a solution of lithium aluminum hydride (98 mg, 2.59 mmol) in 4 mL of dry diethyl ether under ice-cooling. The mixture was heated at reflux for 5 hours with stirring. Then the mixture was hydrolyzed with a dropwise addition of 2 mL water, 2 mL of sodium hydroxide 10% w/v solution, and 6 mL water, under stirring and ice-cooling. The mixture was filtered under vacuum, and the residue was washed twice with diethyl ether.

Another 30 mL of diethyl ether was added to the ethereal filtrate and the solution was extracted with 60 mL (2×30 mL) of hydrochloric acid 6% w/v. The aqueous phase was separated and made alkaline through addition of an excess solid sodium carbonate under ice-cooling. The aqueous phase was extracted twice with 30 mL of dichloromethane. The combined organic extracts were dried (Na$_2$SO$_4$) and evaporated under vacuum, to yield a light yellow colored solid residue of 3-(1-adamantyl)-pentan-3-amine 260. Yield: 10 mg (10.9%); MS: 222.4; $^{13}$C-NMR (200 MHz, CDCl$_3$) δ: 9.90 (CH$_3$), 26.73 (CH$_2$), 29.04 (C$_{3',5',7'}{}^{Ad}$) 36.75 (C$_{4',6',10'}{}^{Ad}$), 37.45 (C$_{2',8',9'}{}^{Ad}$), (C$_{1'}{}^{Ad}$), (C—N).

Preparation of 4-(adamantan-1-yl)heptan-4-amine (261)

Referring to Scheme 8, the Grignard reagent was prepared from magnesium turnings (1.33 g, 55.4 mmol) and allyl bromide (6.1 g, 50.4 mmol) in 60 mL of dry diethyl ether. A solution of 1-adamantanecarbonyl chloride 202 (2 g, 10.1 mmol) in 60 mL of dry diethyl ether was added dropwise to the first solution, under Ar atmosphere and stirring. The reaction mixture was heated at gentle reflux for 4 hours under stirring and Ar atmosphere and an additional 24 hours at room temperature under stirring and Ar atmosphere. The mixture was hydrolyzed with an equal volume of saturated solution of ammonium chloride under ice-cooling. The organic layer was separated and the aqueous phase was extracted with diethyl ether twice. The combined organic phase was washed with water and brine, dried (Na$_2$SO$_4$) and evaporated under vacuum to yield a yellow colored oil residue of 4-(1-adamantyl)-hept-1,6-dien-4-ol 207. Yield: 1.74 g (70%); IR (Film) δ: ν (OH) 3568 cm$^{-1}$ (br s), ν (=C—H) 3074 (s), 3008 (m), ν (C=C) 1636 (s); $^1$H-NMR (400 MHz, CDCl$_3$) δ: 1.70 (q, 12H), 1.99 (s, 3H), 2.28-2.40 (m, 4H), 5.09 (t, 4H), 5.88-5.98 (m, 2H); $^{13}$C-NMR (200 MHz, CDCl$_3$) δ: 28.81 (C$_{3',5',7'}{}^{Ad}$), 36.57 (C$_{4',6',10'}{}^{Ad}$), 37.29 (C$_{2',8',9'}{}^{Ad}$), 39.29 (CH$_2$), 40.34 (C$_{1'}{}^{Ad}$), 76.08 (C—OH), 118.11 (=CH$_2$), 135.82 (—CH=).

The 4-(1-adamant-yl-hept-1,6-dien-4-ol 207 (840 mg, 3.42 mmol) was dissolved in 80 mL of absolute ethanol and the solution was hydrogenated under Adams catalyst (80 mg) for 20 hours. Vacuum filtration of the catalyst and solvent evaporation under vacuum yields a white solid residue of 4-(1-adamantyl)-heptan-4-ol 208. Yield: 720 mg (84.2%); IR (Nujol): ν (OH) 3469 cm$^{-1}$ (br s), $^1$H-NMR (400 MHz, CDCl$_3$) δ: 0.90 (t, 6H), 1.29-1.39 (m, 4H), 1.41-1.50 (m, 4H), 1.65 (q, 12H), 1.98 (s, 3H), 2.17 (s, 1H); $^{13}$C-NMR (200 MHz, CDCl$_3$) δ: 15.29 (CH$_3$), 18.19 (CH$_2$), 28.89 (C$_{3',5',7'}{}^{Ad}$), 36.59 (C$_{4',6',10'}{}^{Ad}$), 36.88 (CH$_2$), 37.39 (C$_{2',8',9'}{}^{Ad}$), 40.28 (C$_{1'}{}^{Ad}$), 41.39 (C—OH).

Trifluoroacetic acid (921 g, 8 mmol) was added dropwise to a mixture of sodium azide (156 mg, 2.4 mmol) in 5 mL of dry dichloromethane at 0° C. under stirring. Stirring was continued for 10 minutes under ice-cooling and a solution of 4-(1-adamantyl)-heptan-4-ol 208 (200 mg, 0.8 mmol) in 7 mL of dry dichloromethane was added dropwise under ice-cooling. The mixture was stirred vigorously for 4 hours under ice-cooling and was made alkaline with ammonia 12% w/v solution under ice-cooling. The organic layer was separated and washed with 40 mL of water twice. The aqueous phase was extracted twice with 40 mL of dichloromethane.

The combined organic extracts were dried (Na$_2$SO$_4$) and evaporated under vacuum to yield 150 mg of a yellow colored oily product consisting of 81 mg (53.8%) of the desired 3-(1-adamantyl)-heptan-4-azide 209 and 69 mg (46.2%) of 4-(1-adamantyl)-hept-3-ene as an elimination byproduct. IR (Flim) ν (=C—H): 3097 cm$^{-1}$ (m), ν (N$_3$) 208 cm$^{-1}$ (s), ν (C=C) 1601 cm$^{-1}$ (w). The crude oily mixture was used without further purification for the LiAlH$_4$ reduction step.

A solution of the crude azide 209 (150 mg) in 3 mL of dry diethyl ether was added dropwise to a solution of lithium aluminum hydride (66 mg, 1.74 mmol) in 3 mL of dry diethyl ether under ice-cooling. The mixture was heated at reflux for 5 hours under stirring. Then the mixture was hydrolyzed with a dropwise addition of 2 mL water, 2 mL of sodium hydroxide 10% w/v solution and 6 mL water under stirring and ice-cooling. The mixture was filtered under vacuum and the residue was washed twice with diethyl ether.

Another 30 mL of diethyl ether was added to the ethereal filtrate and the solution was extracted with 60 mL (2×30 mL) of hydrochloric acid 6% w/v. The aqueous phase was separated and made alkaline by addition of an excess solid sodium carbonate under ice-cooling. The aqueous phase was extracted twice with 30 mL of dichloromethane. The combined organic extracts were dried (Na$_2$SO$_4$) and evaporated under vacuum, to yield a light yellow colored solid residue of 4-(1-adamantyl)-heptan-4-amine 261. Yield (based on azide): 10 mg (13.7%); MS: 250.1; $^1$H-NMR (400 MHz, CDCl$_3$) δ: 0.06 (s, 1H), 0.89 (t, 6H), 1.19-1.41 (m, 10H), 1.61 (t, 12H), 1.98 (s, 3H); $^{13}$C-NMR (200 MHz, CDCl$_3$) δ: 15.45 (CH$_3$), 18.59 (CH$_2$), 29.07 (C$_{3',5',7'}{}^{Ad}$), 36.65 (C$_{4',6',10'}{}^{Ad}$), 37.45 (CH$_2$), 37.97 (C$_{2',8',9'}{}^{Ad}$), 39.53 (C$_{1'}{}^{Ad}$), 56.94 (C—N).

Compounds of Formula VII are shown in Scheme 9.

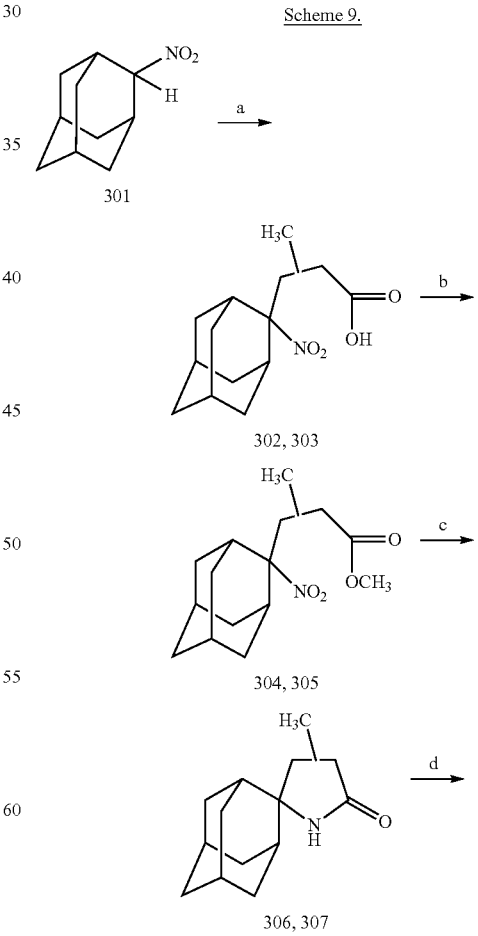

Scheme 9.

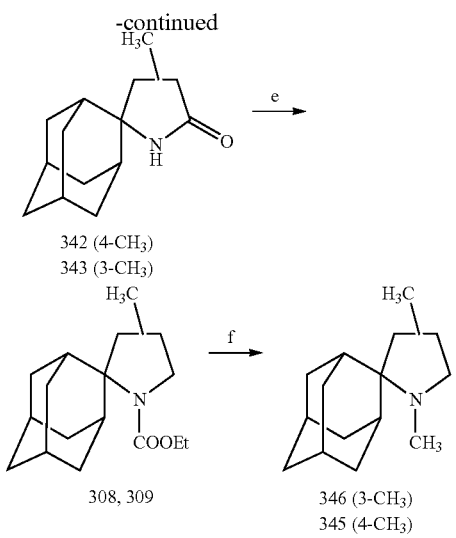

342 (4-CH₃)
343 (3-CH₃)

308, 309

346 (3-CH₃)
345 (4-CH₃)

Reagents and Conditions: (a) i.CH₃CH═CHCO₂Et or CH₂═CH(CH₃)CO₂Et, Triton-B, t-BuOH, 80° C., 12 h; ii. NaOH, EtOH-H₂O 3:1, reflux (301 to 302 56% or 301 to 303 67%); (b) MeOH/HCl(g), 60° C., 6 h (94% for 304 or 70% for 305); (c) H₂/Ni-Raney, EtOH, 50 psi, 60° C., 10 h (83% for 306 or 95% for 307); (d) LiAlH₄, THF, reflux (65 h, 47% for 343 or 46 h, 87% for 342); (e) ClCO₂Et, Et₃N, ether, r.t., 25 h (65% for 308 or 97% for 309); (f) LiAlH₄, THF, reflux 21 h (76% for 346 or 88% for 345).

Preparation of 2- or 3-methyl-3-(2-nitro-2-tricyclo [3.3.1.1³,⁷]decyl) propanoic acid (303) and (302)

To a stirred solution of 2-nitroadamantane 301 (4.0 g, 22.0 mmol) and methyl crotonate or methyl methacrylate (4.4 g, 44.0 mmol) in tert-BuOH (25 mL) was added dropwise a 40% methanolic solution of Triton B (2.4 mL). An exothermic reaction was observed. The reaction mixture was heated to 80° C. for 12 hours, cooled at room temperature and acidified under ice cooling with HCl 6%. The resulting mixture was extracted with ether and the organic phase was washed with water and brine and evaporated under vacuum. The oily residue was treated with a solution of NaOH 1 N (3.5 g in 66 mL EtOH/22 mL water) at 70° C. for 6 hours and the mixture was left overnight at room temperature. After ethanol was evaporated, water was added and the mixture was washed with ether. The aqueous solution was acidified with HCl 18%, and the precipitated acid was filtered off, washed with water, and dried: yield 3.34 g (56%) for 3-methyl derivative 303 or 4.25 g (70%) for 2-methyl derivative 302.

3-methyl derivative 303; mp 165° C. (MeOH); ¹H-NMR (CDCl₃, 400 MHz) δ (ppm) 0.96 (d, 3H, J~7 Hz, CH₃), 1.65-2.05 (m, 13H, 4, 5,6,7,8,9,10-adamantane H, CH₂CO₂H), 2.60-2.80 (m, 3H, 1, 3-adamantane H, CH₂CO₂H), 2.90-3.0 (m, 1H, CHCH₂). Anal. (C₁₄H₂₁NO₄) C, H.

2-methyl derivative 302; mp 177° C. (MeOH); IR (Nujol) ν (C═O) 1689, ν (NO₂) 1530 cm⁻¹; ¹H-NMR (CDCl₃, 400 MHz) δ (ppm) 1.15 (d, 3H, J=7 Hz, CH₃), 1.60-2.10 (m, 13H, 4, 5,6,7,8,9,10-adamantane H, CH₂CH), 2.40-2.60 (m, 3H, 1,3-adamantane H, CH₂CH), 2.70-2.80 (dd, 1H, J~8, 15 Hz, CH₂CH). Anal. (C₁₄H₂₁NO₄) C, H.

Preparation of methyl-2- or 3-methyl-3-(2-nitro-2-tricyclo [3.3.1.1³,⁷]decyl)propanoate (305) or (304)

To a stirred methanolic solution of HCl, resulting from adding 13.5 mL of saturated (43% w/v) methanolic HCl in 100 mL dry MeOH, was added portion wise carboxylic acid 303 or 302 (4.1 g, 15.4 mmol) under ice cooling. The resulting solution was heated to 80° C. for 6 hours and left overnight at room temperature. Methanol was evaporated and ether was added to the oily mixture. The organic solution was washed with water, NaHCO₃ 10% (×2), water, brine and dried (Na₂SO₄). After solvent evaporation the oily ester 305 (3.77 g, 94%) or 304 (4.10 g, 95%) was afforded.

3-methyl derivative 305; IR (Film) ν (C═O) 1730, ν (NO₂) 1531 cm⁻¹; ¹H-NMR (CDCl₃, 400 MHz) δ (ppm) 0.87 (d, 3H, J~7 Hz, 13-CH₃), 1.60-2.0 (m, 13H, 4, 5,6,7, 8,9,10-adamantane H, CH₂CO₂H), 2.55-2.70 (m, 3H, 1,3-adamantane H, CH₂CO₂H), 2.85-2.95 (m, 1H, CHCH₂).

2-methyl derivative 304; mp 177° C. (MeOH); IR (Nujol) ν (C═O) 1742, ν (NO₂) 1536 cm⁻¹; ¹H-NMR (CDCl₃, 400 MHz) δ (ppm) 1.10 (d, 3H, J~7 Hz, α-CH₃), 1.60-2.0 (m, 13H, 4, 5,6,7,8,9,10-adamantane H, CH₂CH), 2.40 (m, 2H, 3-adamantane H, CH₂CH), 2.53 (br s, 1H, 1-adamantane H), 2.68-2.75 (dd, 1H, J~8, 15 Hz, CH₂CH), 3.65 (s, 3H, COOCH₃).

Preparation of 3- or 4-methylspiro[pyrrolidine-2,2'-tricyclo[3.3.1.1³,⁷]decan]-5-one (306) or (307)

A solution of nitroester 305 or 304 (3.73 g, 13.3 mmol) in ethanol (70 mL) was hydrogenated for 10 hours under pressure (50 psi) at 50° C. over Raney-Nickel catalyst. Catalyst was filtered off and the filtrate was evaporated under vacuum to give the solid 3-methyl lactam derivative 306 (2.40 g, 83%) or 4-methyl lactam derivative 307 (2.77 g, 95%).

3-methyl lactam 306; mp 190° C. (MeOH); IR (Nujol) ν (NH) 3201, ν (C═O) 1681 cm⁻¹; ¹H-NMR (CDCl₃, 400 MHz) δ (ppm) 0.98 (d, 3H, J~7 Hz, 3-CH₃), 1.60-2.0 (m, 15H, 4-H, adamantane H), 2.51-2.59 (m, 1H, 3-H), 2.67-2.73 (m, 1H, 4-H), 6.55 (br s, 1H, N—H); ¹³C-NMR (CDCl₃, 50 MHz) δ (ppm) 15.5 (CH₃), 26.4, 26.7 (7', 5'-C), 31.8 (1'-C), 33.3, 33.7 (4', 9'-C), 34.2 (3-C), 34.8, 35.0 (10', 8'-C), 35.7 (6'-C), 39.0 (4-C), 65.3 (2'-C), 176.5 (5-C). Anal. (C₁₄H₂₁NO) C, H.

4-methyl lactam 307; mp 203° C. (MeOH); IR (Nujol) ν (NH) 3207, ν (C═O) 1685 cm⁻¹; ¹H-NMR (CDCl₃, 400 MHz) δ (ppm) 1.20 (d, 3H, J~7 Hz, 4-CH₃), 1.35-1.50 (m, 1H, 3-H), 1.55-1.95 (m, 14H, adamantane H), 2.45-2.60 (m, 2H, 3,4-H), 6.90 (br s, 1H, N—H); ¹³C-NMR (CDCl₃, 50 MHz) δ (ppm) 16.7 (CH₃), 26.6, 26.8 (7'-C, 5'-C), 33.4, 33.7 (4'-C, 9'-C), 34.9, 34.2 (10',8'-C), 35.6 (1'-C), 36.6 (4-C), 37.8 (6'-C), 39.5 (3'-C), 40.9 (3-C), 61.7 (2'-C), 179.5 (5-C). Anal. (C₁₄H₂₁NO) C, H.

Preparation of 3- or 4-Methylspiro[pyrrolidine-2,2'-tricyclo[3.3.1.1³,⁷]decane] (342) or (343)

To a stirred suspension of LiAlH₄ (1.65 g, 43.3 mmol) in dry THF (60 mL) was added dropwise a solution of the lactam 306 or 307 (1.90 g, 8.70 mmol) in dry THF (40 mL). The reaction mixture was refluxed for 65 or 46 hours respectively and then hydrolyzed with water, NaOH (15%) and water under ice cooling. The inorganic precipitate was filtered off and washed with THF, and the filtrate was concentrated in vacuo. The residue was dissolved in ether and extracted with HCl (6%). The aqueous layer was made alkaline with solid Na₂CO₃ and the oily product formed was extracted with ether. The combined ether extracts were washed with water, brine and then dried (Na₂SO₄). After evaporation of the solvent, the residue was flash chromatographed on silical gel (35-70 μm) with ether-methanol 1/1 as an eluent to give 3-methyl pyrrolidine 343 (830 mg, 46.5%) or 4-methyl pyrrolidine 342 (1.52 g, 87%) as an oil.

3-methyl pyrrolidine 343; $^1$H-NMR (CDCl$_3$, 400 MHz) δ (ppm) 0.82 (d, 3H, J~7 Hz, 3-CH$_3$), 1.34-1.40 (m, 1H, 4-H), 1.50-1.81 (m, 11H, 1', 3', 4'eq, 5', 6', 7', 8', 9'eq, 10'eq-H), 1.87 (br d, 1H, J~13 Hz, 10'ax-H), 1.95 (br d, 1H, J~12 Hz, 9'ax-H), 1.99-2.10 (m, 2H, 4'ax-H, 4-H), 2.30-2.38 (m, 1H, 3-H), 2.84-2.88 (m, 1H, 5-H), 2.95-3.20 (m, 1H, 5-H); $^{13}$C-NMR (CDCl$_3$, 50 MHz) δ (ppm) 15.9 (3-CH$_3$), 27.5 (5', 7'-C), 32.5 (4'-C), 33.3 (9'-C), 33.8, 34.2 (3'-C, 1'-C), 34.9 (4-C), 35.2 (8', 10'-C), 36.2 (3-C), 38.3 (6'-C), 42.4 (5-C), 67.8 (2'-C). Hydrochloride: mp 230° C. dec. (EtOH-Et$_2$O); Anal. (C$_{14}$H$_{24}$NCl) C, H.

4-methyl pyrrolidine 342; $^1$H-NMR (CDCl$_3$, 400 MHz) δ (ppm) 0.99 (d, 3H, J~6 Hz, 4-CH$_3$), 1.06-1.13 (m, 1H, 3-H), 1.50-1.85 (m, 12H, 1', 3', 4'eq, 5', 6', 7', 8', 9'eq, 10'-H), 1.95-2.02 (m, 2H, 4'ax, 9'ax-H), 2.07-2.12 (m, 2H, 3,4-H), 2.43-2.48 (dd, 1H, J~8, 10 Hz, 5-H), 3.03-3.08 (dd, 1H, J~7, 10 Hz, 5-H); $^{13}$C-NMR (CDCl$_3$, 50 MHz) δ (ppm) 18.8 (4-CH$_3$), 27.0 (7'-C), 27.2 (5'-C), 33.4 (4'-C), 33.9 (4-C), 34.5 (9'-C), 34.9 (10'-C), 35.8 (8'-C), 37.5 (3'-C), 38.1 (6'-C), 38.7 (1'-C), 45.2 (3-C), 53.3 (5-C), 66.3 (2'-C). Hydrochloride: mp>274° C. (EtOH-Et$_2$O). Fumarate: mp 163° C. dec. (EtOH-Et$_2$O); Anal. (C$_{18}$H$_{27}$NO$_4$) C, H.

Preparation of 1,3- or 1,4-dimethylspiro[pyrrolidine-2,2'-tricyclo[3.3.1.1$^{3,7}$]decane] (346) or (345)

A solution of ethyl chloroformate (530 mg, 4.88 mmol) in dry ether (10 mL) was added dropwise under ice cooling to a stirred solution of the pyrrolidine 342 or 343 (500 mg, 2.44 mmol) and triethylamine (860 mg, 8.56 mmol) in dry ether (15 mL). The mixture was stirred at room temperature for 25 hours. The precipitated triethylamine hydrochloride was filtered off and washed with ether. The filtrate was washed with water, cold HCl 3%, water, dried (Na$_2$SO$_4$) and evaporated in vacuo. After flash chromatography on silical gel (35-70 μm) with ether as an eluent the oily carbamate 308 (400 mg, 64.5%; IR (Film) 1695 cm$^{-1}$) or 309 (656 mg, 97%; IR (Film) 1710 cm$^{-1}$) was obtained, and used without further purification for the preparation of N-methyl derivatives 346 or 345 respectively.

To a stirred suspension of LiAlH$_4$ (274 mg, 7.22 mmol) in dry THF (10 mL) was added dropwise a solution of the carbamate 308 or 309 (400 mg, 1.44 mmol) in dry THF (10 mL). The reaction mixture was refluxed for 21 hours and then hydrolyzed with water, NaOH 15% and water under ice cooling. The inorganic precipitate was filtered off and washed with THF, and the filtrate was concentrated under vacuum. The residue was dissolved in ether and extracted with HCl 6%. The aqueous phase was made alkaline with solid Na$_2$CO$_3$ and the oil formed was extracted with ether. The combined ether extracts were washed with water, brine and dried (Na$_2$SO$_4$). After evaporation of the solvent, the residue was flash chromatographed on silical gel (35-70 μm) with ether as an eluent to afford 1,3-dimethyl pyrrolidine 346 (240 mg, 76%) or 1,4-dimethyl pyrrolidine 345 (278 mg, 88%) as an oil.

1,3-dimethyl pyrrolidine 346; $^1$H-NMR (CDCl$_3$, 400 MHz) δ (ppm) 1.07 (d, 3H, J~7 Hz, 3-CH$_3$), 1.42 (br d, 1H, J~12 Hz, 4'eq-H), 1.50-1.75 (m, 7H, 4, 9'eq, 6', 8'eq, 10'eq-H), 1.76-1.88 (m, 4H, 5', 7', 8'ax, 10'ax-H), 1.98-2.06 (m, 3H, 1', 3', 4-H), 2.11 (br d, 1H, J~12 Hz, 9'ax-H), 2.31-2.40 (m, 1H, 4'ax, 3-H), 2.47 (s, 3H, N—CH$_3$), 2.70-2.76 (m, 1H, 5-H), 3.05-3.10 (m, 1H, 5-H); $^{13}$C-NMR (CDCl$_3$, 50 MHz) δ (ppm) 19.5 (3-CH$_3$), 27.1, 27.5 (7', 5'-C), 29.9 (1'-C), 32.1, 33.2 (4', 9'-C), 34.6 (3', 4-C), 35.1 (8', 10'-C), 37.2 (3-C), 38.4 (6'-C), 39.1 (N—CH$_3$), 52.2 (5-C), 67.8 (2'-C). Fumarate: mp 170° C. (EtOH-Et$_2$O); Anal. (C$_{19}$H$_{29}$NO$_4$) C, H.

1,4-dimethyl pyrrolidine 345; $^1$H-NMR (CDCl$_3$, 400 MHz) δ (ppm) 1.0 (d, 3H, J~7 Hz, 4-CH$_3$), 1.45-1.50 (m, 3H, 4'eq, 9'eq, 3-H), 1.64-1.88 (m, 10H, 1', 3', 5', 6', 7', 8', 10'-H), 1.98 (dd, 1H, J~10, 13 Hz, 3-H), 2.12 (br d, 1H, J~12 Hz, 9'ax-H), 2.21 (br d, 1H, J~13 Hz, 4'ax-H), 2.27 (s, 3H, N—CH$_3$), 2.52 (dd, 1H, J~8, 13 Hz, 5-H), 3.02 (dd, 1H, J~9, 13 Hz, 5-H); $^{13}$C-NMR (CDCl$_3$, 50 MHz) δ (ppm) 21.9 (4-CH$_3$), 27.3, 27.5 (7', 5'-C), 30.9 (4-C), 33.5 (4'-C), 33.7 (3'-C), 33.8 (9'-C), 34.1 (1'-C), 35.1, 35.3 (8', 10'-C), 38.4 (6'-C), 38.5 (N—CH$_3$), 39.1 (3-C), 61.7 (5-C), 71.5 (2'-C). Fumarate: mp 157° C. (EtOH-Et$_2$O); Anal. (C$_{19}$H$_{29}$NO$_4$) C, H.

Compounds of Formula VII are also shown in Scheme 10.

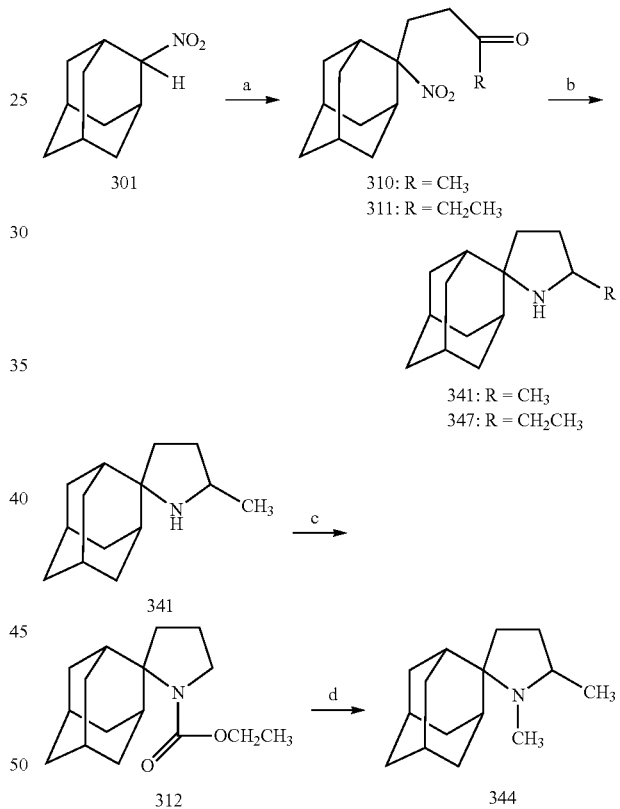

Scheme 10.

301

310: R = CH$_3$
311: R = CH$_2$CH$_3$

341: R = CH$_3$
347: R = CH$_2$CH$_3$

341

312

344

Reagents and Conditions: a) CH$_2$=CHCOR (R = CH$_3$ or C$_2$H$_5$), Amberlyst A-27 (-NR$_3$$^+$OH-), ether, r.t., 10 h (36% for 310, 86% for 311); b) H$_2$/Ni-Raney, EtOH, 50 psi, 50° C., 10 h (92% for 341, 71% for 347). (c) ClCO$_2$Et, Et$_3$N, ether, r.t., 25 h (50%); (d) LiAlH$_4$, THF, reflux, 21 h (53%).

Preparation of 4-(2-nitro-2-tricyclo[3.3.1.1$^{3,7}$]decyl)-2-butanone (310)

A solution of 2-nitroadamantane 301 (2.50 g, 13.8 mmol) and methyl vinyl ketone (970 mg, 13.8 mmol) in ether (20 mL) was stirred at 0° C. for 10 minutes. The hydroxide form of the resin Amberlyst A-27 (3 g) was added, and the mixture was stirred for 15 minutes at 0° C. and 24 hours at room temperature. The resin was filtered off and washed with ether (4×15 mL), and the ether was evaporated under vacuum. The crude product was purified by flash chromatography on silical gel (35-70 µm) using hexane/ether 1:1 as an eluent to give 1.33 g (36%) of the pure ketone 310: mp 75° C. (ether-n-pentane); IR (Nujol) v (C=O) 1721, v (NO$_2$) 1525 cm$^{-1}$; $^1$H-NMR (CDCl$_3$, 400 MHz) δ (ppm) 1.66-1.70 (m, 6H, 5, 6, 7, 8 eq, 10 eq-adamantane H), 1.75-1.85 (m, 4H, 4 eq, 9 eq, 8ax, 10ax-adamantane H), 1.89 (br d, 2H, J~13 Hz, 4ax, 9ax-adamantane H), 2.09 (s, 3H, CH$_3$), 2.17-2.21 (m, 2H, CH$_2$CH$_2$CO), 2.30-2.35 (m, 2H, CH$_2$CH$_2$CO), 2.47 (br s, 2H, 1,3-adamantane H). Anal. (C$_{14}$H$_{21}$NO$_3$) C, H.

Preparation of 5-methylspiro[pyrrolidine-2,2'-tricyclo[3.3.1.1$^{3,7}$]decane] (341)

A solution of nitroketone 310 (1.33 g, 5.30 mmol) in ethanol (30 mL) was hydrogenated for 10 hours under pressure (50 psi) at 50° C. over Raney-Nickel catalyst. Catalyst was filtered off and the filtrate was evaporated under vacuum to give the oily pyrrolidine 341 (1.0 g, 92%).

5-methyl pyrrolidine 341; $^1$H-NMR (CDCl$_3$, 400 MHz) δ (ppm) 1.11 (d, 3H, J~7 Hz, 5-CH$_3$), 1.16-1.28 (m, 1H, 4-H), 1.47 (br s, 1'-H), 1.55-1.60 (m, 4H, 1', 3', 4'eq, 9'eq-H), 1.61-1.87 (m, 11H, 3, 4, 5', 6', 7', 8', 10'-H), 1.93 (br d, 1H, J=13 Hz, 4'ax-H), 2.04 (br d, 1H, J~13 Hz, 9'ax-H), 3.12-3.18 (m, 1H, 5-H); $^{13}$C-NMR (CDCl$_3$, 50 MHz) δ (ppm) 22.0 (5-CH$_3$), 27.2 (7'-C), 27.3 (5'-C), 34.0 (4-C), 33.9 (4'-C), 34.2 (9'-C), 34.8 (3-C), 36.2 (10'-C), 36.8 (8'-C), 36.8 (3'-C), 38.2 (6'-C), 39.5 (1'-C), 52.8 (5-C), 66.4 (2'-C). Fumarate: mp 191-193° C. dec. (EtOH-Et$_2$O); Anal. (C$_{18}$H$_{27}$NO$_4$) C, H.

Preparation of 5-ethylspiro[pyrrolidine-2,2'-tricyclo[3.3.1.1$^{3,7}$]decane] (347)

The synthesis of 347 began with Michael addition between 2-nitroadamantane 301 and ethyl vinyl ketone using NR$_3$$^+$OH$^-$ resin as basic catalyst (see Ballini, R.; Marziali, P.; Mozzicafreddo, A. *J. Org. Chem.* 1996, 61, 3209-3211; Cainelli, G.; Manescalchi, F. *Synthesis* 1976, 472-473); this resin was prepared by treating the commercial —NR$_3$$^+$Cl$^-$ form of Amberlyst A-27 resin with aqueous NaOH 1 M. The application of this methodology afforded nitroketone 311 (900 mg, 3.59 mmol) which was hydrogenated under Ni-Raney to produce the 2-ethylpyrrolidine 347: yield 557 mg (71%); $^1$H-NMR (CDCl$_3$, 400 MHz) δ (ppm) 0.91 (t, 3H, J~7 Hz, 5-CH$_2$CH$_3$), 1.17-1.40 (m, 2H, 4-H, 5-CH$_2$CH$_3$), 1.45-1.55 (m, 2H, 5-CH$_2$CH$_3$, 1'H), 1.57-1.63 (m, 3H, 3', 4' eq, 9' eq-H), 1.65-1.90 (m, 11H, 3, 4, 5', 6', 7', 8', 10'-H), 1.96 (br d, 1H, J~13 Hz, 4'ax-H), 2.01 (br d, 1H, J~13 Hz, 9'ax-H), 2.95-3.10 (m, 2H, 5-H); $^{13}$C-NMR (CDCl$_3$, 50 MHz) δ (ppm) 11.7 (5-CH$_2$CH$_3$), 27.3 (7'-C), 27.5 (5'-C), 30.2 (5-CH$_2$CH$_3$), 31.4 (4-C), 34.2 (4'-C), 34.3 (9'-C), 35.0 (3-C), 35.7 (10'-C), 36.0 (8'-C), 37.0 (3'-C), 38.3 (6'-C), 39.6 (1'-C), 59.2 (5-C), 65.6 (2'-C). Fumarate: mp 191-193° C. dec. (EtOH-Et$_2$O); Anal. (C$_{19}$H$_{29}$NO$_4$) C, H.

Preparation of 1,5-Dimethylspiro[pyrrolidine-2,2'-tricyclo[3.3.1.1$^{3,7}$]decane] (344)

A solution of ethyl chloroformate (476 mg, 4.40 mmol) in dry ether (10 mL) was added dropwise under ice cooling to a stirred solution of the pyrrolidine 341 (450 mg, 2.20 mmol) and triethylamine (780 mg, 3.30 mmol) in dry ether (15 mL). The mixture was stirred at room temperature for 25 hours. The precipitated triethylamine hydrochloride was filtered off and washed with ether. Then the filtrate was washed with water, cold HCl 3%, and water, dried (Na$_2$SO$_4$), and evaporated in vacuo. After flash chromatography on silical gel (35-70 µm) with ether as the eluent the oily carbamate 312 (290 mg, 50%; IR (Film) 1711 cm$^{-1}$) was obtained, and used without further purification for the preparation of the N-methyl derivative 344.

To a stirred suspension of LiAlH$_4$ (367 mg, 9.68 mmol) in dry DME (10 mL) was added dropwise a solution of the carbamate 312 (670 mg, 2.40 mmol) in dry DME (10 mL). The reaction mixture was refluxed for 24 h and then hydrolyzed with water, NaOH 15% and water under ice cooling. The inorganic precipitate was filtered off and washed with DME, and the filtrate was concentrated in vacuo. The residue was dissolved in ether and extracted with HCl 6%. The aqueous phase was made alkaline with solid Na$_2$CO$_3$ and the oily product formed was extracted with ether. The combined ether extracts were washed with water and brine, and dried (Na$_2$SO$_4$). After evaporation of the solvent, the residue was flash chromatographed on silical gel (35-70 µm) with methanol/ethyl acetate 1:1 as an eluent to afford pyrrolidine 344 (280 mg, 53%) as an oil.

1,5-dimethyl pyrrolidine 344; $^1$H-NMR (CDCl$_3$, 400 MHz) δ (ppm) 1.37 (d, 3H, J~7 Hz, 5-CH$_3$), 1.34-1.52 (m, 2H, 4'eq, 9'eq-H), 1.60-1.87 (m, 13H, 3, 4, 1', 3', 5', 6', 7', 8', 10'-H), 2.13 (s, 3H, N—CH$_3$), 2.12-2.25 (m, 2H, 4'ax, 9'ax-H), 3.03-3.15 (m, 1H, 5-H); $^{13}$C-NMR (CDCl$_3$, 50 MHz) δ (ppm) 20.4 (5-CH$_3$), 27.3 (7'-C), 27.5 (5'-C), 30.3 (4-C), 31.0 (3-C), 33.2, 33.3 (1', 3'-C), 33.5 (4', 9'-C), 34.7 (N—CH$_3$), 35.1 (10'-C), 35.3 (8'-C), 37.7 (6'-C), 38.4 (5'-C), 70.6 (2'-C). Fumarate: mp 135° C. (EtOH-Et$_2$O); Anal. (C$_{19}$H$_{29}$NO$_4$) C, H.

General.

Melting points were determined using a Buchi capillary apparatus and are uncorrected. IR spectra were recorded on a Perkin-Elmer 833 spectrometer. $^1$H and $^{13}$C NMR spectra were recorded on a Bruker DRX 400 and AC 200 spectrometer at 400 and 50 MHz, respectively, using CDCl$_3$ as solvent and TMS as internal standard. Carbon multiplicities were established by DEPT experiments. 2D NMR experiments (HMQC and COSY) were used for the elucidation of the structures of intermediates and final products. Microanalyses were carried out by the Service Central de Microanalyse (CNRS) France, and the results obtained had a maximum deviation of ±0.4% from the theoretical value. The assignments of $^1$H and $^{13}$C signals were achieved by the combined use of DEPT, 2D COSY, NOESY and HMQC experiments. 2D experiments were run on a Bruker-DRX 400 MHz operating at 400.13 for $^1$H. A relaxation delay of 2 s was used for all experiments. For the NOESY experiments a mixing time of 1.5 s was used.

Biological Testing Methods

Cells and media: Tissue used for preparation of virus stock cultures, virus infectivity titrations, and miniplaque drug assays were Madin-Darby Canine Kidney (MDCK) cells (ATCC CCL 34). The cell culture growth medium used was Dulbecco's Modified Eagle's Medium (DMEM, Sigma-Aldrich) supplemented with 0.11% sodium bicarbonate, 5% Cosmic calf serum (Hyclone), 10 mM HEPES buffer, and 50 µg/ml of gentamycin. For culture of virus stocks and virus infectivity assays 0.125% bovine serum albumin (BSA, Sigma-Aldrich) was substituted for the Cosmic calf serum.

Virus: Influenza A virus, the 2009 pandemic strain (A/California/07/2009), was provided by Dr. Don Smee, Utah State University. Trypsin added to BSA-supplemented media for virus activation was TPCK-treated bovine pancreas trypsin (Sigma-Aldrich). A virus stock culture (passage 1) was prepared in MDCK cells in a 150 cm$^2$ culture flask. The cells were planted in growth medium and incubated until the cell monolayer was at 90% confluency. The monolayer was washed with medium containing no serum (serumless medium), then renewed with BSA medium containing 2.5 μg/ml of trypsin. The culture was infected with 1 ml of the virus inoculum obtained from Dr. Smee, then incubated at 33° C. At 2 days post-infection the culture had reached complete cytopathic effect. Detached cells and cell debris were removed by low speed centrifugation (600×g for 5 min.), the supernatant aliquoted in 1 ml quantities, then frozen at −80° C. for storage. For virus titration, aliquots of the stock were thawed and dilution series were inoculated in MDCK cultures in shell vials and virus-infected cells detected by immunofluorescence. The anti-viral monoclonal antibody used for all immunofluorescence tests was FITC-labeled Influenza A Reagent produced by Light Diagnostics and obtained from Millipore.

Miniplaque assay. In cell culture, mini-plaques consist of single infected cells, double or multiple infected cells contiguously linked, that are observed microscopically and identified by immunofluorescence using FITC-labeled monoclonal antibody against viral protein. Antiviral activity of test drugs were detected in cultures exposed to drug by assessing inhibition of viral protein synthesis (virus replication) as measured by reduction in number of mini-plaques. The tests were performed in MDCK cells. Cells were grown on 12-mm glass cover slips in shell vials (Sarstadt) to a cell density of 80-99% confluency in 1 ml of DMEM growth medium per vial. Prior to infection the cultures were washed with serumless media. The serumless medium was replaced with 1 ml per vial of DMEM containing BSA at a concentration of 0.125%. Test drugs at appropriate concentrations were added to the cultures and allowed to equilibrate with the media. Stock virus was thawed and appropriate concentrations of virus (contained in BSA media) were then exposed to 1.0 μg/ml of trypsin for 30 minutes at room temperature, then added to the cultures. Replicate cultures were included at each dilution step of test chemical. Control cultures containing no antiviral drug were included in each assay. The cultures were then incubated at 33° C. overnight. Cultures were washed with phosphate buffered saline (PBS) within the shell vials, fixed in −80° C. acetone, then stained with anti-Influenza A, FITC-labeled monoclonal antibody (Millipore, Billerica, Mass., USA). Possible drug toxicity in culture was assessed by microscopic observation of cytologic changes and cell multiplication rates.

$EC_{50}$ determinations were carried out with a fluorescence microscope by counting miniplaques (clusters of infected cells, typically 100-300 per cover slip in control samples and fewer in cultures treated with active drugs) in a confluent MDCK monolayer on a cover slip at drug concentrations of 50 μM, 20 μM, 10 μM, 5 μM, and, if necessary, 2 μM. From two to four replicate cultures were included at each drug concentration step. Plaque counts, C(D), (including controls and weighted by the standard error of the count for each concentration), were fitted, using the Levenberg-Marquardt algorithm (in KaleidaGraph from Synergy Software, Reading, Pa., USA), to the sigmoidal function:

$$C(D) = \frac{C_0}{1 + \frac{D}{EC_{50}}}$$

with D being the drug concentration and C0 and EC50 being free parameters. The standard error of the EC50, used as reported by the software, reflects the uncertainties due to variances in the counts at all concentrations, including the controls.

Resistance testing: Cultured MDCK cells bathed in 3-5 μM drug were exposed to the usual quantities of virus. After the cultures developed complete cytopathic effects, the cultures were terminated. The medium, containing virus, was then collected by low speed centrifugation. Dose-response curves utilizing the mini-plaque technique were performed on the recovered virus for determination of the EC50 against the potentially mutated virus. An increase represents resistance development. The virus was then used for the next passage of cell culture inoculation and the process repeated until strong resistance developed.

Liposome Test Methods

Peptide Expression and Purification:

The M2(22-62) construct used in these liposome assays included the transmembrane domain, with the S31N mutation installed by site-directed mutagenesis, and post-TM amphipathic helix. The construct, expressed in transfected E. coli BL21 (DE3), was comprised of an N-terminal 6-histidine tag followed by the large, soluble maltose binding protein, then a TEV-protease cleavage site, and finally the insoluble M2(22-62, S31N) peptide. The fusion protein was collected from the bacterial membrane fraction by solubilization with dodecylmaltoside, and purified via affinity chromatography with a Ni-NTA column.

The peptide was cleaved from the fusion protein with TEV protease for 20 h. The reaction mixture was precipitated with trichloroacetic acid and lyophilized. The cleaved M2(22-62) peptide was solubilized using methanol and the concentration determined by absorbance at 280 nm using a generic extinction coefficient (1 ml mg$^{-1}$ cm$^{-1}$). It contains a fragment of the TEV cleavage site (Ser, Asn, Ala) at the N-terminus, such that the total length is 44 amino acids, with a calculated molecular weight of 5014.9 Da.

Liposome Preparation:

Liposomes were prepared by mixing chloroform-suspended E. coli polar lipid extract (67% phosphatidylethanolamine, 23.2% phosphatidylglycerol, 9.8% cardiolipin, average molecular weight: 798 Da; Avanti Polar Lipids, Alabaster, Ala., USA) with the methanol-suspended M2(22-62) S31N peptide. The solvent was then evaporated under a steady stream of N2 gas. The resulting clear lipid film was placed in a vacuum for 1-2 h to remove any remaining traces of solvent. Internal buffer (50 mMKCl, 50 mMK$_2$HPO$_4$, 50 mMKH$_2$PO$_4$, pH 8.0, 320 mOsm) was added to the thin film, vortexed to form liposomes, then extruded through a 100-nm pore-size polycarbonate filter (Liposofast membrane extruder, Avestin, Ottawa, Canada) at 50-60° C. After extrusion, samples were divided for matched-pair drug block assessment. Test compounds were added to liposome and external buffers at a concentration of 100 μM. The average vesicle diameter was found to be 145±15 nm by dynamic light scattering (Brookhaven Instruments, Holtsville, N.Y., USA).

Experimental Protocol:

Liposomes were diluted 100-fold into 3 ml of external buffer, 165 mM NaCl, 0.05 mM KH$_2$PO$_4$/K$_2$HPO$_4$, pH 7, 320 mOsm, in a 1-dram vial. Because [K$^+$] is negligible in the external buffer, the dilution creates a 100× gradient in [K$^+$] across the liposome membrane, which yields an electrical potential of −110 mV for a K+-selective membrane at room temperature (after compensating for K+ activity coefficients). A pH electrode (Accumet combination electrode with calomel reference, model 13-620-293, Fisher Scientific, Houston, Tex., USA) was used to measure proton movement into or out of the liposomes throughout the experiment. The external buffer was acidified to a pH of 6.5 with 0.1 M HCl under stirring after liposome dilution and allowed to equilibrate for 2 minutes. Valinomycin (Sigma-Aldrich Corp.) was then added to the solution to a concentration of 30 nM to render the membrane dominantly permeable to $K^+$ and produce the membrane potential. Two minutes after valinomycin, CCCP was added to a concentration of 1.67 µM. Finally, two calibration aliquots of 30 nEq HCl were added for calibration of the earlier pH changes to yield nEq $H^+$ influx rates. Valinomycin and CCCP were again added in the same quantities after complete CCCP-gradient neutralization to evaluate the time course and size of the direct impact of the two compounds and their and their ethanol carrier on the bath pH. Experiments with drugs were compared to controls with protein and no drug, no protein and drug, and no protein/no drug.

The initial proton influx was determined by fitting the rise in external buffer pH after valinomycin addition with a least squares fit of a straight line. Up to 6 independent measurements with drug were averaged and normalized by the non-drug controls, which were grouped together from all experiments. Experiments with excessively permeable liposomes due to lipid oxidation, as judging from the total signal size (after considering post-hoc control artifacts), were excluded.

Test Results $EC_{50}$ values were measured by infecting MDCK cells with influenza A(S31N) in the presence or absence of test compounds, and then counting the number of miniplaques formed. Scheme A shows the compounds tested. Scheme B shows variants of compound 7 that were also tested and found to be effective. Proton uptake was determined using liposome assays with the M2 S31N peptide.

Scheme A.

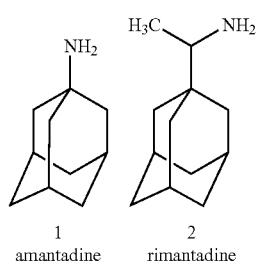

1  
amantadine 2  
rimantadine

3

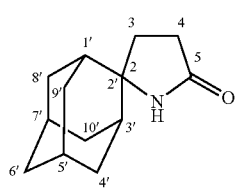

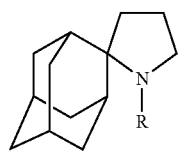

4: R = H
5: R = CH₃

-continued

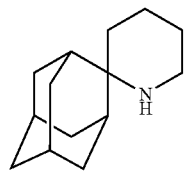
6

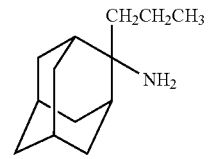
7

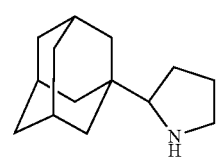
8

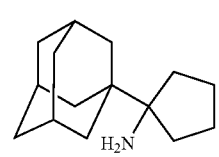
9

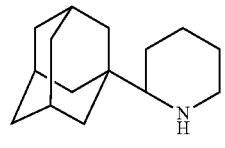
10

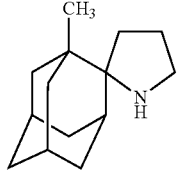
11

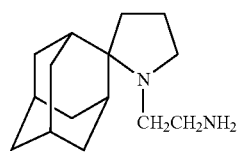
12

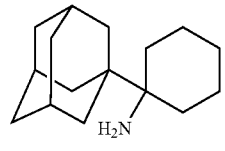
13

Scheme B.

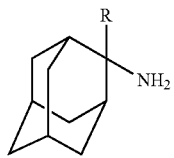

14: R = H
15: R = CH₃
16: R = CH₂CH₃
17: R = CH₂CH₂CH₂CH₃
18: R = CHCH(CH₃)₂
101: R = CH₂CH₂CH₂CH₂CH₂CH₃
19: R = Ph
20: R = CH₂Ph

Scheme C.

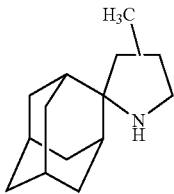

342 (4-CH₃)
343 (3-CH₃)

344

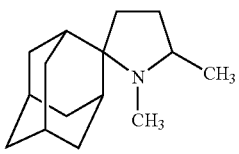

345 (4-CH₃)
346 (3-CH₃)

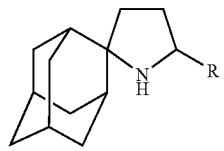

341 R = CH₃
347 R = CH₂CH₃

Miniplaque $EC_{50}$ values and their respective standard error from dose-response testing based on least-squares fitting of single-site binding curves are shown for tested compounds in Table I. N is the number of assay counts fitted for each drug. Measurements were made using the A/California/07/2009 virus. The H+ uptake rate by liposomes, comprised of 0.1 mg M2 22-62 (S31N) and 20 mg lipid per ml electrolyte, is given as percent of drug free control uptake rate±SD (%-control) (N) (drug free control: 9.7±2.0 (40) H+/tetramer/s) at a drug concentration of 100 μM in the internal and external electrolytes. The standard deviation of the %-control was calculated using propagation of errors. The strong reduction in $EC_{50}$ and H+ uptake give clear indications that the drugs of Scheme A are efficacious against Influenza A/California/07/2009, whereas amantadine and rimantadine are not, consistent with the fact that this strain contains the amantadine-resistant S31N variation in M2. For comparison, wild type (WT) viral strains that are sensitive to amantadine and rimantadine in the clinic are typically blocked in cell culture with an $EC_{50}$ less than 10 μM and the associated M2 is blocked to less than 10% of drug free control in the liposome assay.

TABLE I

| Compound # | $EC_{50}$ ± SE (μM) (N) | H+ Uptake Rate ± SD (%) (N) |
|---|---|---|
| Amantadine (1) | 242 ± 91 (13) | 77 ± 29 (8) |
| Rimantadine (2) | 106 ± 41 (13) | ND |
| 3 | 15.6 ± 3.3 (13) | ND |
| 4 | 7.6 ± 1.8 (13) | 6.4 ± 1.8 (6) |
| 5 | 7.9 ± 1.5 (16) | ND |
| 6 | 19.8 ± 2.5 (15) | 1.3 ± 5.7 (6) |
| 7 | 4.71 ± 0.92 (20) | 24 ± 17 (6) |
| 8 | 15.4 ± 2.4 (16) | 12 ± 13 (5) |
| 9 | 0.79 ± 0.14 (18) | 11 ± 25 (3) |
| 10 | 7.0 ± 1.2 (14) | ND |
| 11 | 36.0 ± 17.1 (17) | 17 ± 8.7 (6) |
| 12 | 2.66 ± 0.33 (17) | 11 ± 18 (4) |
| 13 | 3.62 ± 0.49 (20) | ND |

Additional $EC_{50}$ assay values with respective standard error ranges are shown for additional viral strains tested, obtained commercially, and compounds from Scheme B in Table II and from Scheme C in Table III. $EC_{50}$ (μM)±its standard error from mini-plaque testing for dose-response or single-dose screens, using cultured MDCK cells, based on least-squares fitting of single-site binding curves. N is the number of assay counts fitted. Experiments with N=2 are based on replicate 50 μM screens (except for 9, which were based on replicate 5 μM screens), with a single control (N=4) for each virus. Row M2 gives variations from the WT amantadine-binding site, if any. In human illness, these amantadine-resistant variants are primarily S31N, but rare instances of L26F, V27A, V27T, A30T, and G34E are also observed. No microscopic evidence of cytotoxicity to MDCK cells was detected after 18 hour exposure at 50 μM for any of the drugs in Scheme A, B, or C except with compound 101, where a 5 μM dose was used instead. The $EC_{50}$ values of amantadine 1 and rimantadine 2, known to be inactive against H1N1 (2009), and other cases where $EC_{50} \geq 24$ μM are bolded in Table II. Again, clinical efficacy can reasonably be expected when the $EC_{50}$ in cell culture assay is below 10 μM. Hence, A/PR/8/34 is amantadine resistant, whereas the WT strains from Taiwan and Victoria are not. Table II shows that most of the compounds from Scheme B are effective against both the amantadine-insensitive strains in the first two columns of results AND against the amantadine-sensitive strains in the last two columns. These data also show that some drugs are most effective with one of the strains and others with others. The strain in the middle column, an amantadine-insensitive S31N virus, is not inhibited well by any of these drugs, but 15, 16, and 101 show some inhibitory effect. Table III shows that compounds from Scheme C are similar in efficacy against A/California/07/2009 to those in Tables I and II with 341 being less effective than the others. Therefore, sets of selected compounds from the invention, or further developments of the scaffolds, hold promise in clinical therapeutics.

TABLE II

| Comp # | A/Calif/07/09 (H1N1) M2 S31N | A/PR/8/34 (H1N1) V27T/S31N | A/WS/33 (H1N1) S31N | A2/Taiwan/1/64 (H2N2) WT | A/Victoria/3/75 (H3N2) WT |
|---|---|---|---|---|---|
| 1   | 240 ± 90 (13)   | 24 ± 3.5 (21)   | 24 ± 1.1 (21)  | 0.34 ± 0.01 (21) | 2.8 ± 0.3 (16)  |
| 2   | 110 ± 40 (13)   | 3.3 ± 0.5 (2)   | 310 ± 140 (2)  | 1.6 ± 0.3 (2)    | 0.53 ± 0.07 (18)|
| 14  | 150 ± 30 (20)   | 3.8 ± 1.0 (2)   | 110 ± 15 (2)   | 0.8 ± 0.3 (2)    | 3.3 ± 0.9 (2)   |
| 15  | 54 ± 2 (20)     | 0.4 ± 0.4 (2)   | 19 ± 4 (2)     | 0.5 ± 0.5 (2)    | 2.0 ± 0.4 (2)   |
| 16  | 25 ± 3 (21)     | 1.8 ± 0.9 (2).  | 23 ± 3 (2)     | 0.8 ± 0.3 (2)    | 2.0 ± 0.4 (2)   |
| 7   | 4.7 ± 0.9 (20)  | 0.5 ± 0.2 (2)   | 390 ± 8 (2)    | <0.24 (2)        | 23 ± 8 (2)      |
| 17  | 8.5 ± 0.6 (20)  | 0.3 ± 0.3 (2)   | 355 ± 4 (2)    | 1.5 ± 0.3 (2)    | 4 ± 1 (2)       |
| 18  | 8.0 ± 0.3 (21)  | 0.3 ± 0.5 (2)   | 210 ± 40 (2)   | 0.4 ± 0.1 (2)    | 13 ± 2 (2)      |
| 101 | 0.13 ± 0.02 (2) | 0.07 ± 0.09 (2) | 13.0 ± 3.6 (2) | 1.5 ± 0.3 (2)    | 1.1 ± 0.1 (2)   |
| 19  | 21 ± 2 (21)     | <0.3 ± 0.5 (2)  | 86 ± 20 (2)    | 0.2 ± 0.2 (2)    | 8 ± 1 (21)      |
| 20  | 8.6 ± 0.8 (21)  | 1.2 ± 1.1 (2)   | 280 ± 150 (2)  | 0.2 ± 0.3 (2)    | 18 ± 2 (21)     |
| 259 | 24 ± 1.9 (2)    | <0.2 ± 0.2 (2)  | 300 ± 115 (2)  | 1.1 ± 0.1 (2)    | 3.4 ± 1.7 (2)   |

TABLE III

| Comp # | A/Calif/07/09 (H1N1) M2 S31N |
|---|---|
| 341 | 34 ± 4 (2) |
| 342 | 9.5 ± 1.6 (12) |
| 343 | 7.2 ± 2.0 (2) |
| 344 | 7.7 ± 2.0 (2) |
| 345 | 7.0 ± 0.8 (2) |
| 346 | 10.2 ± 1.2 (2) |
| 347 | 8.7 ± 1.7 (2) |

Resistance Testing

Resistance testing for selected compounds was also measured. As shown in Table IV, cultured MDCK cells were bathed in a concentration corresponding to approximately the $EC_{50}$ concentration, which were exposed to the usual quantities of virus for 3-4 days (approximately 5-7 virus replication cycles per passage). After that time, the cultures developed cytopathic effects and the cultures were terminated. The medium containing virus was then collected by low speed centrifugation. Dose-response tests utilizing the mini-plaque technique were performed on the recovered virus for determination of the $EC_{50}$ against the potentially mutated virus. An increase in the $EC_{50}$ above the original value represents resistance development. This process was repeated for each passage.

Resistance development in an H3N2 strain in the presence of 5 µM amantadine 1 was explored using an amantadine-sensitive H3N2 virus and found to be complete during a single 3-4 day passage ($1^{st}$ column of results in Table IV). In contrast, the A/California/07/2009 strain that bears the amantadine-insensitive M2 S31N was very slow to develop in the presence of 7 (5 µM), a mixture of 9, 10, and 19 (each at their $EC_{50}$ concentration), and of 13 (3.6 µM). In each case, resistance development took more than 6 passages, i.e. about 3 weeks, longer than the usual course of therapeutic treatments in humans.

TABLE IV

| Passage # | 1 (5 µM) H3N2[a] $EC_{50}$ ± S.E. (µM) | 7 (5 µM) H1N1[b] $EC_{50}$ ± S.E. (µM) | 9, 10, 19 H1N1[b] $EC_{50}$ ± S.E.[c] (µM) | 13 (3.6 µM) H1N1[b] $EC_{30}$ ± S.E. (µM) |
|---|---|---|---|---|
| 0  | 2.8 ± 0.3 | 4.7 ± 0.9 | 1.0x ± 0.2x | 3.8 ± 0.5 |
| 1  | Inactive  | 5.4 ± 1.4 | —           | —         |
| 2  | Inactive  | 3.7 ± 0.5 | —           | —         |
| 5  | N.D.      | 2.1 ± 1.6 | —           | —         |
| 6  | —         | —         | 1.5x ± 0.1x | 12 ± 0.8  |
| 8  | —         | 19 ± 1    | —           | 26 ± 2    |
| 10 | —         | 76 ± 9    | 7.9x ± 0.8x | 33 ± 3    |
| 12 | —         | 150 ± 120 | N.D.        | N.D.      |

In Table IV above, the following applies to the information displayed in the table: $EC_{50}$ ± SE was calculated (µM or multiple of 1x) (N = 21) after designated passage (incubation) stages;
[a] H3N2: Influenza AA/Victoria/3/75.
[b] H1N1: Influenza A/California/07/2009;
[c] for this incubation mixture, the drug component concentrations were each equal to their $EC_{50}$s: 9 (0.36 µM), 10 (2.8 µM), 19 (9.2 µM); $EC_{50}$s are in units of original-cocktail multiples; Inactive: no miniplaque reduction by 50 µM amantadine 1; Dash: not tested; N.D.: passaging not done.

In Table IV above, the following applies to the information displayed in the table: $EC_{50}$±SE was calculated (µM or multiple of 1x) (N=21) after designated passage (incubation) stages; [a]H3N2: Influenza A/Victoria/375. [b]H1N1: Influenza A/California/07/2009; [c]for this incubation mixture, the drug component concentrations were each equal to their $EC_{50}$s: 9 (0.36 µM), 10 (2.8 µM), 19 (9.2 µM); $EC_{50}$s are in units of original-cocktail multiples; Inactive: no miniplaque reduction by 50 µM amantadine 1; Dash: not tested; N.D.: passaging not done.

In the amantadine-H3N2 system, drug resistance appeared after one passage, with no detectable activity of amantadine 1 against the progeny from passage 1 or passage 2 at 50 µM. In contrast, the amantadine-resistant A/California/07/2009 strain did not develop resistance for ~3 weeks of passaging, which demonstrates a powerful resilience of these compounds against viral resistance development. This impact on amantadine-resistant virus has important therapeutic potential. The passage 12 7-resistant mutant was subsequently tested and found to be sensitive to compound 13 ($EC_{50}$ 10±2 µM) and, to a lesser extent, to compound 9 $EC_{50}$ 22±2 µM).

Prophetic Examples

The compound numbering in schemes 5, 6, and 7 is intended to be unique to the prophetic examples. Any duplication of numbering with non-prophetic examples in Schemes A, B, C, and 1-10 is inadvertent.

Scheme 5. (Prophetic examples)

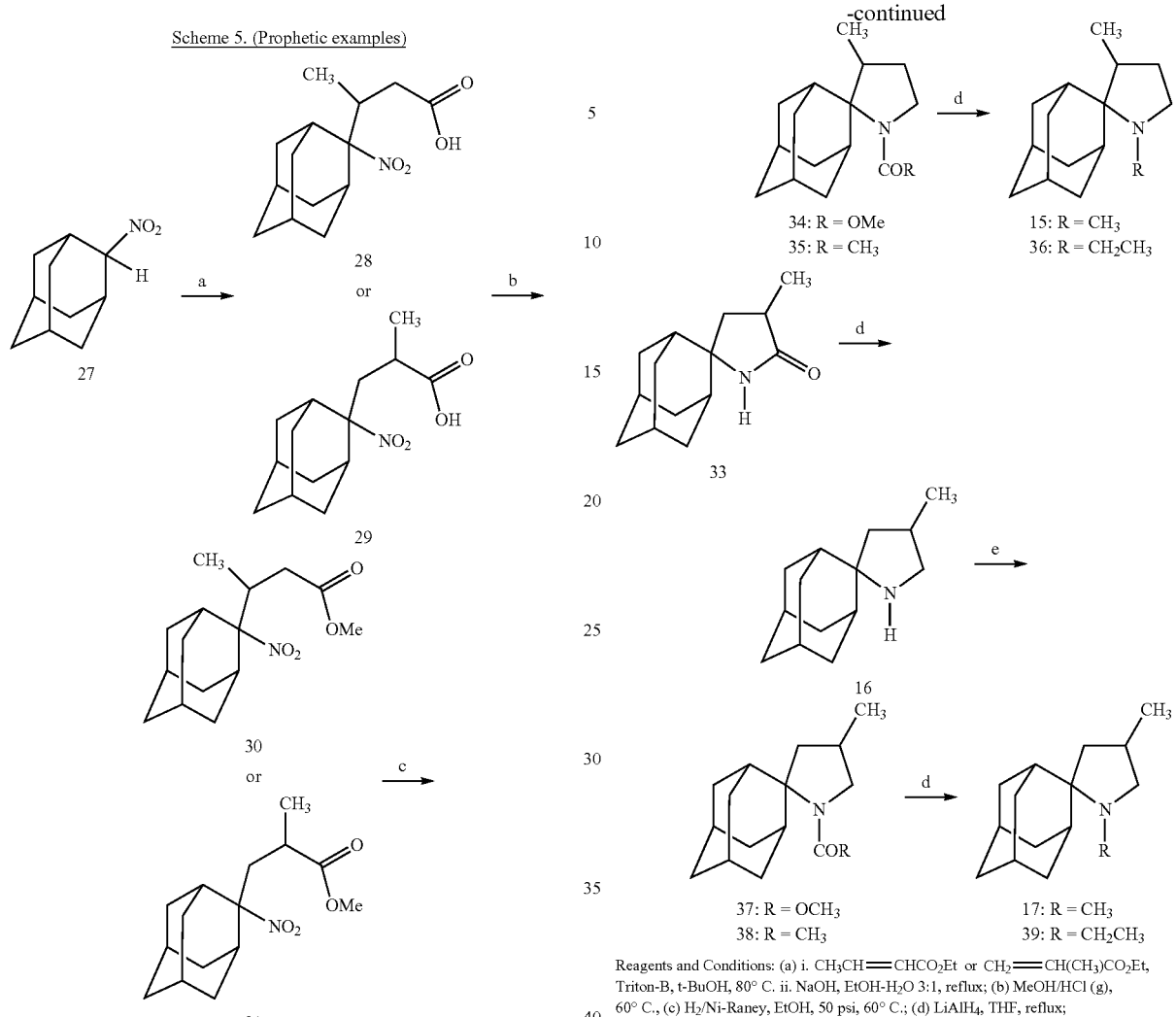

Reagents and Conditions: (a) i. CH₃CH=CHCO₂Et or CH₂=CH(CH₃)CO₂Et, Triton-B, t-BuOH, 80° C. ii. NaOH, EtOH-H₂O 3:1, reflux; (b) MeOH/HCl (g), 60° C., (c) H₂/Ni-Raney, EtOH, 50 psi, 60° C.; (d) LiAlH₄, THF, reflux; (e) ClCOOEt or CH₃COCl, Et₃N, THF, r.t.

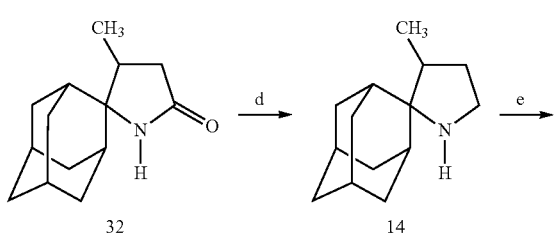

The synthesis of the 5-methyl and 5-ethylspiro[pyrrolidine-2,2′-adamantanes] 18, 42 (see Scheme 6) can start from the Michael addition between 2-nitroadamantane 27 and methyl or ethyl vinyl ketone using NR₃⁺OH⁻ resin as basic catalyst; this resin can be prepared by treating the commercial —NR₃⁺Cl⁻ form of Amberlyst A-27 resin with aqueous NaOH 1 M. The application of this methodology can afford nitroketones 40 or 41 which can be hydrogenated under Ni-Raney to produce the 5-alkylpyrrolidines 18 or 42. The preparation of N-alkyl derivatives 45, 46, 49, 50 can be realized as previously depicted in Scheme 5.

Scheme 6. (Prophetic examples)

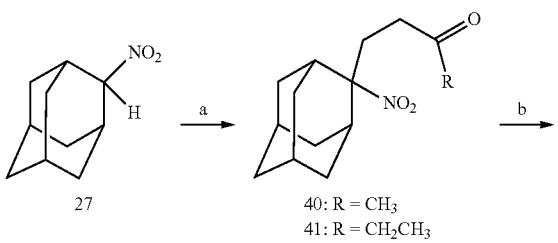

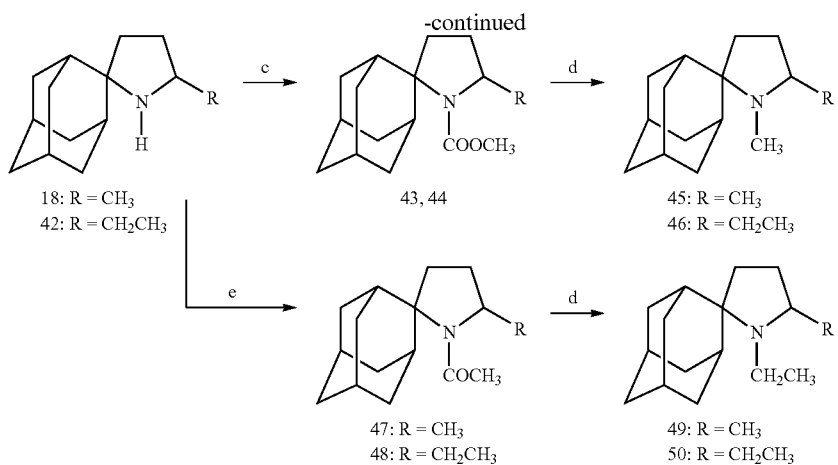

Reagents and Conditions (a) CH$_2$═CHCOCH$_2$CH$_3$, Amberlyst A-27 (─NR$_3$ +OH$^-$), ether, r.t.; (b) H$_2$/Ni-Raney, EtOH, 50 psi, 50° C.; (c) ClCO$_2$Et or CH$_3$COCl, Et$_3$N, ether, r.t.; (d) LiAlH$_4$, THF, reflux.

Prophetic Preparation of 2-alkyl-2-adamantanamines 60-63 and their N-methyl Derivatives 68-71

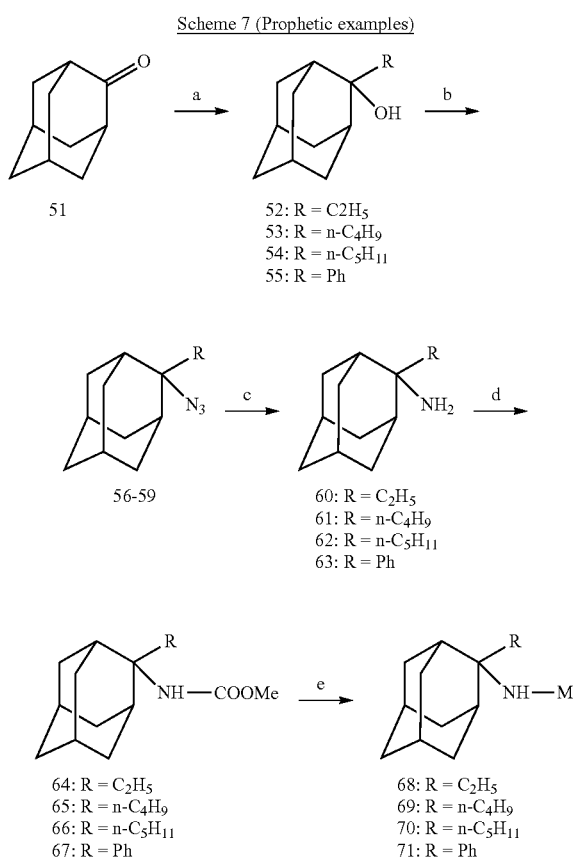

Reagents and Conditions: (a) RMgI, ether, THF, r.t., 2 h then NH$_4$Cl/H$_2$O or RLi, Ar, THF, 0° C., 2 h then NH$_4$Cl/H$_2$O; (b) NaN$_3$, H$_2$SO$_4$ 70% w/w, CHCl$_3$, 0° C. then r.t. (c) LiAlH$_4$, ether, r.t., 24 h; (d) ClCO$_2$Et or CH$_3$COCl, Et$_3$N, ether, r.t.; (e) LiAlH$_4$, THF, reflux.

The invention claimed is:

1. A compound of formula I or pharmaceutically acceptable salts thereof, $$\text{(I)}$$

(structure with H$_2$N- and -R$^1$ on adamantane)

wherein R$^1$ is selected from C$_5$-C$_8$ alkyl, C$_1$-C$_5$ alkylenearyl, and aryl, wherein the aryl of alkylenearyl and aryl are optionally substituted with C$_1$-C$_4$ alkyl, provided that the compounds of formula I exclude compounds where R$^1$ is phenyl.

2. The compound or pharmaceutically acceptable salts of claim 1, wherein R$^1$ is C$_5$-C$_8$ alkyl.

3. A pharmaceutical composition comprising a compound or a pharmaceutically acceptable salt thereof of claim 1 and a pharmaceutically acceptable carrier.

4. The compound of claim 1, wherein R$^1$ is C$_5$-C$_8$ alkyl.

5. The compound of claim 1 or pharmaceutically acceptable salts thereof wherein R$^1$ is C$_6$-C$_8$ alkyl.

6. The compound of claim 1 or pharmaceutically acceptable salts thereof wherein R$^1$ is aryl optionally substituted with C$_1$-C$_4$ alkyl.

7. The compound of claim 1 or pharmaceutically acceptable salts thereof wherein R$^1$ is C$_1$-C$_5$ alkylenearyl optionally substituted with C$_1$-C$_4$ alkyl.

8. The compound of claim 1 or pharmaceutically acceptable salts thereof wherein R$^1$ is aryl optionally substituted with methyl.

9. The compound of claim 1 or pharmaceutically acceptable salts thereof, of the structure

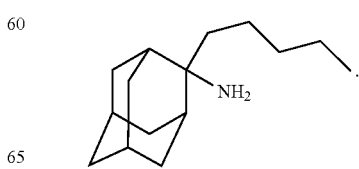

10. A pharmaceutical composition comprising a compound or a pharmaceutically acceptable salt thereof of claim 9 and a pharmaceutically acceptable carrier.

11. The compound of claim 1 or pharmaceutically acceptable salts thereof, of the structure

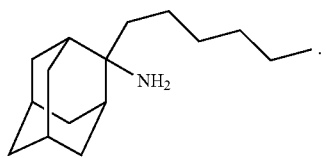 [SMILES: CCCCCCC1(N)C2CC3CC(C2)CC1C3]

12. A pharmaceutical composition comprising two or more compounds or pharmaceutically acceptable salts thereof of claim 1 and a pharmaceutically acceptable carrier.

13. The compound or pharmaceutically acceptable salts of claim 1, wherein $R^1$ is n-pentyl, n-hexyl, n-heptyl, or n-octyl.

* * * * *